(12) United States Patent
Darcy et al.

(10) Patent No.: US 8,852,895 B2
(45) Date of Patent: Oct. 7, 2014

(54) MACROCYCLIC DERIVATIVE AND ASSEMBLIES FORMED THEREFROM

(75) Inventors: Raphael Darcy, Dublin (IE); Caitriona O'Driscoll, Cork (IE)

(73) Assignees: University College Dublin, National University of Ireland (IE); University College Cork, National University of Ireland (IE)

( * ) Notice: Subject to any disclaimer, the term of this patent is extended or adjusted under 35 U.S.C. 154(b) by 594 days.

(21) Appl. No.: 13/002,067

(22) PCT Filed: Jul. 6, 2009

(86) PCT No.: PCT/EP2009/058521
§ 371 (c)(1),
(2), (4) Date: Dec. 30, 2010

(87) PCT Pub. No.: WO2010/000869
PCT Pub. Date: Jan. 7, 2010

(65) Prior Publication Data
US 2011/0124103 A1    May 26, 2011

(30) Foreign Application Priority Data
Jul. 4, 2008 (GB) .................... 0812226.9

(51) Int. Cl.
*A61K 47/40* (2006.01)
*A61K 31/724* (2006.01)

(52) U.S. Cl.
USPC .......................................................... 435/97

(58) Field of Classification Search
USPC .......................................................... 435/97
IPC .......... A61K 47/48969,49/189, 51/1268, 8/738, A61K 9/1652, 9/205, 9/5036, 9/5161
See application file for complete search history.

(56) References Cited

FOREIGN PATENT DOCUMENTS

| WO | 01/83564 | 11/2001 |
|----|----------|---------|
| WO | 2008/009831 | 1/2008 |

OTHER PUBLICATIONS

Diaz-Moscoso (Chem Commun 2008, 2001-2003.*
Ortega-Caballero (Organic Letters 10(22) 5143-5146, 2008.*

* cited by examiner

*Primary Examiner* — David Lukton
(74) *Attorney, Agent, or Firm* — Nixon Peabody LLP

(57) ABSTRACT

The present invention is directed to a macrocyclic derivative which is formed by modification of a macrocycle. The invention further relates to assemblies formed by the self-assembly of such macrocyclic derivatives in aqueous solvent, and includes bilayer vesicles, micelles, monolayers, nanoparticles, colloidal assemblies and surface-coated assemblies.

13 Claims, 2 Drawing Sheets

MACROCYCLIC DERIVATIVE AND ASSEMBLIES FORMED THEREFROM

CROSS-REFERENCE TO RELATED APPLICATIONS

This application is a 371 National Phase Entry Application of International Application No. PCT/EP2009/058521 filed Jul. 6, 2009, which designates the U.S., and which claims the benefit of priority of Great Britain Application No. 0812226.9 filed Jul. 4, 2008, the contents of which are incorporated herein by reference in their entirety.

INTRODUCTION

The present invention relates to a macrocyclic derivative which is formed by modification of a macrocycle. The invention further relates to assemblies formed by the self assembly of such macrocyclic derivatives in aqueous solvent, and includes bilayer vesicles, micelles, monolayers, nanoparticles, colloidal assemblies and stacked assemblies.

In the specification the term "macrocycle" refers to a linear oligomer, where the ends of the oligomer are joined to form a ring. A cyclodextrin is a type of macrocycle and in the specification the term "cyclodextrin" refers to macrocyclic oligosaccharides composed of D-(+)-glucopyranosyl units linked $\alpha(1\rightarrow4)$. The three main members of the cyclodextrin family consist of six, seven and eight glucose units and are known as $\alpha$-, $\beta$- and $\gamma$-cyclodextrins respectively. In the specification the terms "macrocyclic derivative" or "cyclodextrin derivative" refer to a macrocycle or cyclodextrin which has been modified by the addition, deletion or substitution of one or more groups on the molecule.

It is well known to modify macrocycles such as cyclodextrins with hydrophilic groups and lipophilic groups at certain positions to provide cyclodextrin or macrocyclic derivatives having elaborated amphiphilicity. The resultant derivatives are generally capable of forming types of assemblies expected of amphiphilic derivatives and these assemblies can be used for the delivery of many chemical and biological compounds.

The amphiphilicity of the derivative can be tailored to suit the particular compound to be delivered, however the hydrophilic-hydrophobic balance of the derivative must also be considered as this is one of the most important criteria for water-solubility and self assembly. Thus there is a need for a macrocyclic derivative with modified amphilicity which is capable of self assembly in aqueous solution to form a number of different types of assemblies, and which when assembled can deliver a wider range of compounds.

STATEMENTS OF INVENTION

According to a general aspect of the invention, there is provided a macrocyclic derivative having a primary and a secondary side, the derivative consisting of units of the formula:

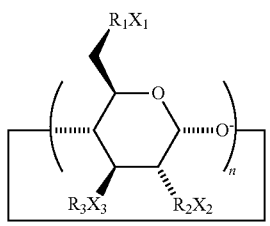

wherein the primary side is hydrophilic and is occupied by the $R_1X_1$ groups; and the secondary side is occupied by the $R_2X_2$ and the $R_3X_3$ groups;
wherein:
n is an integer from 6 to 8;
$X_1$, $X_2$, $X_3$ are linking groups;
$R_1$ and one of $R_2$ or $R_3$ are hydrophilic groups; and
the other of $R_2$ or $R_3$ is a lipophilic group comprising one or more of an aliphatic chain, an alicyclic, an aromatic, and a heterocyclic group or combinations thereof and is of a sufficient size such that the secondary side is overall lipophilic.

In one embodiment of the invention, $R_1$ and $R_3$ provide groups which are polar and/or capable of hydrogen bonding and are selected from the group comprising one or more of H, $(CH_2)_{2-4}OH$, $CH_2CH(CH_3)OH$, $OCH_3$, $OCH_2CH_3$, $CH_2CH_2CH_3$ a cation, an anion, any pharmaceutically acceptable ion, a polymer and a dendrimeric group, a poly (ethylene glycol) (PEG) chain. The remaining constituents are described below.

According to a first aspect of the invention, there is provided a macrocyclic derivative having a primary and a secondary side, the derivative consisting of units of the formula:

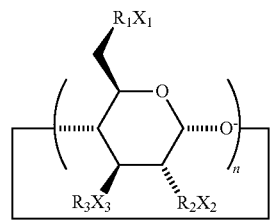

wherein the primary side is hydrophilic and is occupied by the $R_1X_1$ groups;
and the secondary side is occupied by the $R_2X_2$ and the $R_3X_3$ groups;
wherein:
n is an integer from 6 to 8;
$X_1$, $X_2$, $X_3$ are linking groups;
$R_1$ and $R_3$ are hydrophilic groups wherein $R_1$ comprises an amine group and $R_3$ is selected from H, $(CH_2)_{2-4}OH$, $CH_2CH(CH_3)OH$, $(CH_2)_{0-2}CH_3$ and $CO(CH_2)_{0-2}CH_3$;
$R_2$ is a lipophilic group comprising one or more of an aliphatic chain, an alicyclic, an aromatic, and a heterocyclic group or combinations thereof, whether saturated or unsaturated, such that the number of lipophilic atoms in $R_2$ exceeds the number of non-lipophilic atoms in $R_3$ causing the secondary side to be lipophilic.

The macrocyclic derivative of the invention can self assemble with other macrocyclic derivatives of this type to form a number of different types of assemblies in aqueous solvent. The primary side is generally oriented outwards in these assemblies, and this provides a number of different advantages. Specifically, in some types of assemblies such as vesicles or nanoparticles, it is useful to allow modification of the derivatives after assembly. This is easier to achieve with the derivatives of this invention; as is well known for cyclodextrins, the groups on the primary side are easier to modify selectively and these are more accessible for rapid chemical reaction. Additionally, as the hydrophilic groups will always be turned outwards, this allows the targeting of the assemblies to specific cells or organs by the incorporation of receptor-specific groups of atoms such as folate, peptides, or cell-recognition molecules such as antibodies, into the hydrophilic groups. This can further require the synthesis of more elaborate structures. It is therefore an advantage to have the polar groups, which in contrast to the lipophilic groups will require great elaboration, on the primary side of the macrocycle.

The amphiphilic nature of the assemblies enables favourable interactions with a number of biological and chemical compounds such as biological cell membranes, nucleic acids or analogues thereof (including DNA, RNA) and a number of drugs.

A still further advantage, is that in the case of the formation of micelles, as the secondary side of the derivative is occupied by both lipophilic and hydrophilic groups, it is envisaged that this will allow the attachment and delivery of both lipophilic and hydrophilic compounds and thus a wider range of compounds can be delivered within the core of the micelle. The main advantage of the secondary side being overall lipophilic, but having both hydrophilic and lipophilic groups, is that this provides both the best solubility and most suitable molecular shape for the formation of different types of assemblies in aqueous solvent.

In one embodiment of the invention, the lipophilic group $R_2$ contains at least 4 carbon atoms.

In a further embodiment of the invention, the lipophilic group $R_2$ further comprises one or more hetero atoms selected from the group comprising oxygen, nitrogen and sulfur.

In a still further embodiment of the invention, the lipophilic group $R_2$ further comprises a functional group selected from one or more of ethers, esters, carbamates, ketones, thioethers, thioesters, thioketones, sulfanyl, disulfide, sulfonyl, sulfoxy, sulfones, triazoles and amides.

As above $R_3$ is ideally selected from H, $(CH_2)_{2-4}OH$, $CH_2CH(CH_3)OH$, $(CH_2)_{0-2}CH_3$ and $CO(CH_2)_{0-2}CH_3$.

Accordingly, in this situation $X_1$ is ideally O. Furthermore, in order for the macrocyclic derivative to be polar $R_3$ should have a small number of carbons relative to $R_2$. Thus, when $R_2$ contains at least 4 carbon atoms, $R_3$ should ideally have a smaller number of carbons. $R_3$ may also be selected from methyl, ethyl or propyl.

In a particularly preferred embodiment of the invention, $R_1$ comprises an amine group and $X_3R_3$ is an OH group.

The advantage of $R_1$ providing an amine group is that the amine group is positively charged in water and thus can neutralise the multiple anionic groups in molecules such as DNA or an oligonucleotide to condense them into compact nanoparticles and encapsulate them for delivery. For example, $R_1$ may be selected from one of the following $(CH_2)_2$ $NH_2$, $NH(CH_2CH_2NH_2)_2$ or peptides with basic amino groups such as -$Arg_8$ or -PEG-$Arg_8$. Other examples are given in the following table.

In one embodiment of the invention, $X_1$, $X_2$ and $X_3$ are independently selected from the group comprising a simple covalent bond or an atom or radical with a valency of at least 2.

In this embodiment of the invention, $X_1$, $X_2$ and $X_3$ further comprise one or more of ethers, esters, carbonates, ketones, thioethers, thioesters, thioketones, sulfanyl, disulfide, sulfonyl, sulfoxy, sulfones, triazoles and amides. The use of a suitable linkage group makes it possible to connect lipophilic or polar groups selectively to either one, or to two, of the 6- or 2- or 3-positions.

Ideally, $X_1$ comprises a poly(ethylene) glycol (PEG) group. In this embodiment of the invention, the PEG group is a straight chain or branched group with one or more of a glycosyl, an oligosaccharide, a peptide, a glycopeptide, a protein, an antibody and any other targeting group attached thereto. The advantage of $X_1$ comprising a PEG group is that the PEG group increases the systemic circulation time of the resultant bilayer vesicle or multi-layered structure thus ensuring better delivery. A further advantage of the PEG group is that its length can be chosen so that it acts as a spacer group positioning the targeting group at the optimum distance from the macrocycle for binding to a receptor.

According to particularly preferred embodiment of the invention, the macrocyclic derivative comprises the following combinations of $R_1X_1$, $R_2X_2$ and $R_3X_3$ groups:

| $R_1X_1$ | $R_2X_2$ | $R_3X_3$ |
|---|---|---|
| —S(CH$_2$)$_2$NH$_2$•TFA (trifluoroacetic acid) | —O(CH$_2$)$_3$S—R where R is selected from the following:<br>(CH$_2$)$_2$—COOCH$_3$,<br>(CH$_2$)$_2$—COOC$_6$H$_{12}$,<br>(CH$_2$)$_2$—COOC$_8$H$_{17}$,<br>(CH$_2$)$_2$—COOC$_{12}$H$_{25}$,<br>CH$_2$)$_2$—COOC$_{16}$H$_{33}$,<br>(CH$_2$)$_2$—COOCH$_2$C$_6$H$_5$,<br>C$_{3-16}$H$_{7-33}$ | OR where R is selected from the following:<br>H, methyl, ethyl, propyl,<br>(CH$_2$)$_{2-4}$OH,<br>CH$_2$CH(CH$_3$)OH,<br>CO(CH$_2$)$_{0-2}$CH$_3$ |
| —N(CH$_2$CH$_2$NH$_2$)$_2$•TFA$_3$ | —O(CH$_2$)$_3$S—R where R is selected from the following:<br>(CH$_2$)$_2$—COOCH$_3$,<br>(CH$_2$)$_2$—COOC$_6$H$_{12}$,<br>(CH$_2$)$_2$—COOC$_8$H$_{17}$,<br>(CH$_2$)$_2$—COOC$_{12}$H$_{25}$,<br>CH$_2$)$_2$—COOC$_{16}$H$_{33}$,<br>(CH$_2$)$_2$—COOCH$_2$C$_6$H$_5$,<br>C$_{3-16}$H$_{7-33}$ | OR, where R is selected from the following:<br>H, methyl, ethyl, propyl,<br>(CH$_2$)$_{2-4}$OH,<br>CH$_2$CH(CH$_3$)OH,<br>CO(CH$_2$)$_{0-2}$CH$_3$ |
| -triazole-Arg$_8$•TFA$_8$ where Arg is D- or L-arginine | —O(CH$_2$)$_3$S—R where R is selected from the following:<br>(CH$_2$)$_2$—COOCH$_3$,<br>(CH$_2$)$_2$—COOC$_6$H$_{12}$,<br>(CH$_2$)$_2$—COOC$_8$H$_{17}$, | OR, where R is selected from the following:<br>H, methyl, ethyl, propyl,<br>(CH$_2$)$_{2-4}$OH,<br>CH$_2$CH(CH$_3$)OH, |

-continued

| $R_1X_1$ | $R_2X_2$ | $R_3X_3$ |
|---|---|---|
|  | $(CH_2)_2$—$COOC_{12}H_{25}$, $CH_2)_2$—$COOC_{16}H_{33}$, $(CH_2)_2$—$COOCH_2C_6H_5$, $C_{3-16}H_{7-33}$ | $CO(CH_2)_{0-2}CH_3$ |
| -triazole-PEG-Arg$_8$, TFA$_8$ where PEG is polyethylene glycol | —$O(CH_2)_3S$—R where R is selected from the following: $(CH_2)_2$—$COOCH_3$, $(CH_2)_2$—$COOC_6H_{12}$, $(CH_2)_2$—$COOC_8H_{17}$, $(CH_2)_2$—$COOC_{12}H_{25}$, $CH_2)_2$—$COOC_{16}H_{33}$, $(CH_2)_2$—$COOCH_2C_6H_5$, $C_{3-16}H_{7-33}$ | OR, where R is selected from the following: H, methyl, ethyl, propyl, $(CH_2)_{2-4}OH$, $CH_2CH(CH_3)OH$, $CO(CH_2)_{0-2}CH_3$ |

While there are several methods known for introducing lipophilic groups at positions 2 and 3 simultaneously, for example by etherification or esterification, to create an overall lipophilic secondary side, the present invention advantageously provides a method for the introduction of lipophilic groups at the 2-position only.

According to the invention, there is also provided two methods for the efficient synthesis of the pure amphiphilic cyclodextrins described above.

In general terms, the macrocycle is protected at the 6-position using a bulky substituent to allow for direct synthesis at the 2-position. The group at the 2-position is substituted with the desired lipophilic group $R_2X_2$ in two stages the second of which takes place either before (the first method) or after (the second method) deprotection of the 6-position to allow for introduction of the hydrophilic group $R_1X_1$ at this position. The group at the 3-position may finally be optionally modified.

According to this aspect of the invention, there is provided a method for making a macrocyclic derivative, preferably as defined above, comprising the steps of:
  (i) protecting a macrocycle at the 6-position using a reagent $R_4X$ where X is a chemical leaving group specific for introduction of a sterically bulky substituent $R_4$ at the 6-position;
  (ii) substituting H at the 2-position with $R_5$ using a reagent $R_5X$, where X is a chemical leaving group specific for introduction of a non-bulky group $R_5$ at the 2-position and $R_5$ is also a reactive group;
  (iii) deprotection of the 6-position with the simultaneous or subsequent introduction of a chemical leaving group or a group amenable to 1,3 dipolar addition, which is then displaced (in the case of the leaving group) or used for addition by a chemically active form of the group $R_1$;
  wherein an additional step of adding a lipophilic moiety to $R_5$ to complete the lipophilic group $A_2$ occurs either before or after step (iii).

The method as described above may also comprise as a further step the optional modification of the group at the 3-position.

According to this aspect of the invention, there is also provided a macrocyclic derivative made in accordance with the above method.

According to one embodiment of this aspect of the invention $R_4X$ is selected from tert-butyldimethylsilyl chloride, p-toluene-sulfonyl chloride and/or other reagents which introduce bulky substituents. Thus, the protecting group may be any type of bulky substituent such as for example, tert-butyldimethylsilyl (TBDMS), trimethylsilyl (TMS), triisopropylsilyl (TIPS), tosyl or other suitable protecting group.

According to another embodiment of this aspect of the invention $R_5$ is selected from groups such as allyl or propargyl and the reagent $R_5X$ includes allyl bromide or propargyl bromide.

According to yet another embodiment of this aspect of the invention the lipophilic moiety is $CH_3(CH_2)_nS$ radical; or $CH_3(CH_2)_nOCOCH_2CH_2S$ radical where n=0, 6, 8, 12, 16; or $C_6H_5OCOCH_2CH_2S$ radical.

According to a further embodiment of this aspect of the invention the chemical leaving group is bromide or iodide or p-toluene sulfonyl (tosyl) and the group amenable to 1,3 dipolar addition is azide.

According to another embodiment of this aspect of the invention the chemically active form of the group $R_1$ is $RS^-$ (thiolate anion) such as $NH_2(CH_2)_2S^-$; or the amines $NH(CH_2CH_2NH_2)_2$ or $NH(CH_2CH_2NH_2)_2$; or for 1,3 addition, N-propargyl-Arg$_8$ or O-propargyl-PEG-Arg$_8$ may be used.

Ideally, the group at the 3-position is ideally modified by reaction with an epoxide or alkyl halide to etherify, or by reaction with an acid chloride or anhydride to esterify.

According to the invention, there is also provided a bilayer vesicle formed from the self-assembly in aqueous solvent of the macrocyclic derivatives of the invention.

According to the invention, there is further provided a micelle formed from the self-assembly in aqueous solvent of the macrocyclic derivatives of the invention.

According to the invention, there is also provided a monolayer formed from the self-assembly in aqueous solvent of the macrocyclic derivatives of the invention.

According to the invention, there is further provided a nanoparticle formed from the self-assembly in aqueous solvent of the macrocyclic derivatives of the invention.

According to the invention, there is still further provided a colloidal assembly formed from the self assembly in aqueous solvent of the macrocyclic derivatives of the invention.

According to the invention, there is yet still further provided a stacked assembly formed by molecular stacking in aqueous solvent of the macrocyclic derivatives of the invention.

According to the invention, there is still further provided a surface-coated assembly formed from the self-assembly in aqueous solvent of one or more of the macrocyclic derivatives of the invention coated with a further macrocyclic derivative of the invention. Ideally, such a surface-coated assembly is formed by amphiphilic or electrostatic interaction.

According to the invention, there is still further provided a surface-coated assembly formed from the self-assembly in aqueous solvent of one or more of the macrocyclic derivatives of the invention coated with a polyamine, peptide, protein, oligosaccharide, polysaccharide, antibody and/or antibody fragment. Ideally, such a surface-coated assembly is formed by amphiphilic or electrostatic interaction.

According to the invention, there is still further provided a surface-coated assembly formed from the self-assembly in aqueous solvent of one or more of the macrocyclic derivatives of the invention coated with a cholesterol, adamantane and/or other lipid derivative. Ideally, such a surface-coated assembly is formed by host-guest inclusion.

According to the invention, there is still further provided a composition comprising a nucleic acid, nucleotide or nucleotide analogue $Nuc_n$ (n=1,2,3, ... 50); and one or more macrocyclic derivatives or an assembly or surface-coated assembly of the invention. Such a composition is ideal for use in the enhancement of the delivery of a nucleic acid, nucleotide or nucleotide analogue to cells, preferably mammalian cells.

According to the invention, there is still further provided a method for in-vitro transfer of a guest molecule into biological cells, comprising the treatment of a suspension of biological cells with a derivative or assembly or surface-coated assembly of the invention wherein contact between the suspension of the biological cells and the derivative and/or assembly effects the transfer of the guest molecule into the biological cells.

Ideally, the guest molecule is a nucleic acid, nucleotide or nucleotide analogue $Nuc_n$ (n=1,2,3, ... 50). Preferably, the treatment occurs for 1 to 72 hours.

DETAILED DESCRIPTION OF THE INVENTION

The present invention will now be described with reference to the following figures.

Figure 1:
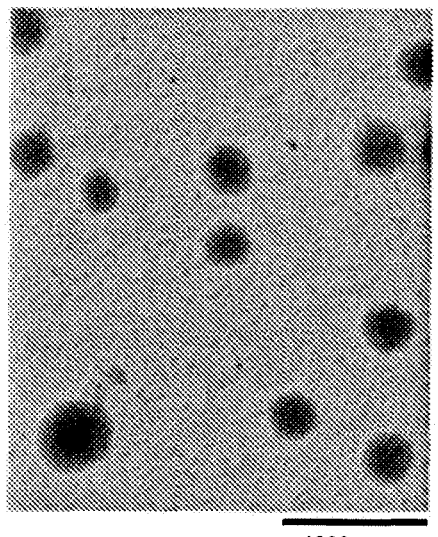
FIG. 1 shows the TEM results of the formation of bilayer vesicles of heptakis[6-(2'-aminoethylthio)-2-O-octyloxycarbonylethylsulfanylpropyl]-β-cyclodextrin trifluoroacetic acid salt according to Example 3.

The cyclodextrin, macrocycle and resultant derivatives comprise a primary side and a secondary side. The primary side comprises the $R_1$ group, and the position which this group occupies is referred to as the 6-position on the cyclodextrin according to IUPAC nomenclature. The secondary side comprises the $R_2$ and $R_3$ groups, and the positions which these groups occupy are referred to as the 2- and 3-positions respectively.

There are two main methods for modifying a macrocycle to provide a macrocyclic derivative. In the first scheme, the macrocycle is protected at the 6-position using a bulky substituent to allow for direct synthesis at the 2-position. The group at the 2-position is substituted with the desired group followed by deprotection of the 6-position to allow for additional synthesis to occur at that position. The group at the 3-position is optionally modified.

In the second method, after protection at the 6-position as above, the 2-position is substituted with a group such as allyl or propargyl which can subsequently be converted into the desired lipophilic group, then the polar group is introduced by the necessary chemical procedure at the 6-position. The group already introduced at the 2-position is now converted to the desired lipophilic group. The group at the 3-position is optionally modified.

It will be appreciated, that the schemes described above have been found to be particularly suitable for providing the derivatives of the invention, however, modification using other acceptable schemes would also be possible.

The protecting group may be any type of bulky substituent such as for example, tert-butyldimethylsilyl (TBDMS), trimethylsilyl (TMS), triisopropylsilyl (TIPS), p-toluenesuolfonyl (tosyl), or other suitable protecting group.

The 6-position can be occupied by an OH, $O(CH_2)_{2-4}OH$, $OCH_2CH(CH_3)OH$, $OCH_3$, $OCH_2CH_3$, $OCH_2CH_2CH_3$ (where $X_1$ is O), any amine group, a cation, an anion, any pharmaceutically acceptable ion, a polymer, a dendrimeric group, and a PEG chain. The PEG group may be a straight chain or a branched group having one or more of a glycosyl, an oligosaccharide, a peptide, a glycopeptide, a protein, an antibody and a targeting group attached. Preferably, the 6-position is occupied by an amine group which could include groups such as $(CH_2)_2NH_2$ or $NH(CH_2CH_2NH_2)_2$, or peptides with basic amino groups such as -$Arg_8$ or -PEG-$Arg_8$.

The presence of a hydrophilic or polar group at the 6-position is particularly important for initial variation at the stage of its incorporation into the amphiphilic cyclodextrin or for later modification, for example by covalent attachment of, or by complexation with, groups or molecules which will act to target the assembly to cell receptors. The addition of the amine group to the 6-position of the cyclodextrin is a preferred modification as the resultant derivative can form both bilayer vesicles and multi-layered structures with oligonucleotides.

The negatively charged groups at the 6-position are particularly suitable for coating and neutralising the surface charge of molecular assemblies formed by cationic cyclodextrins with oligonucleotides or DNA.

A particularly preferred modification has the amine group in its protonated form, for neutralisation of the anionic charges of the oligonucleotides, leading to condensation and encapsulation of DNA or RNA.

Lipophilic groups at the 2-positions will generally consist of at least four carbons. Examples of these groups could include, aliphatic, alicyclic, aromatic and heterocyclic groups, saturated or unsaturated, or combinations thereof. The lipophilic group may also contain one or more hetero atoms, such as oxygen, nitrogen and sulfur. Furthermore, the lipophilic group can include ethers, esters, carbamates, ketones, thioethers, thioesters, thioketones, sulfanyl, disulfide, sulfonyl, sulfoxy, sulfones, triazoles and amides.

The conditions for the addition of each of the groups would depend on the type of group that is being added. It is further conceivable that the 2-position could be protected and then the 3 position modified. The 2-position could then be subsequently deprotected and modified with a different group.

The group at the 3-position can either be an unmodified OH or can be modified by substituting with another hydrophilic group. Suitable hydrophilic groups $OR_3$ (where $X_3$ is O) that could occupy the 3-position include groups such as H, $(CH_2)_{2-4}OH$, $CH_2CH(CH_3)OH$, $CH_2CH(CH_3)OH$, $CO(CH_2)_{0-2}CH_3$, a cation, an anion, any pharmaceutically acceptable ion, a polymer, a dendrimeric group and a poly (ethylene glycol) chain. It has previously been found to be difficult to fully modify this position as it is sterically hindered. Therefore, attempted modification of this position has been found to lead to impurities, that is, some product molecules with unmodified 3-positions. Modification of this position can however be carried out after protection of the 2-position.

Ideally, the group at the 3-position $R_3$ is selected from H, $(CH_2)_{2-4}OH$, $CH_2CH(CH_3)OH$, $(CH_2)_{0-2}CH_3$ and $CO(CH_2)_{0-2}CH_3$.

It had not been previously considered possible for modified cyclodextrins having groups with different amphiphilicity in the 2- and 3-positions to self-assemble to form micelles, vesicles and other molecular assemblies. On the contrary, one would have expected that this would lead to hydrophilic-lipophilic balancing problems with the design of the amphiphile, since there would have been equal numbers of each type of group on one side of the macrocycle, and this would be expected to lead to poor properties of self assembly in aqueous solution. It has been found however that by incorporating a lipophilic group having at least 4 carbons that this renders the secondary side of the derivative sufficiently lipophilic to allow the self-assembly of the cyclodextrin in aqueous solution to form multilayered structures, and further allows the encapsulation of a wider range of compounds. Furthermore, the introduction of lipophilic groups at the 2-positions only creates amphiphiles which are soluble in water for purposes of self assembly.

The macrocyclic derivatives of the present invention can self assemble in aqueous solvent to form a number of assemblies and in particular bilayer vesicles, micelles, monolayers, nanoparticles, colloidal assemblies, and surface-coated assemblies In the case of bilayer vesicles, the primary hydrophilic side of the derivatives faces outwards and due to the bilayer structure, the primary hydrophilic side of the corresponding derivative face inwards to form a hydrophilic water core. The vesicles can therefore be used to deliver hydrophilic molecules, such as DNA, RNA, siRNA, within their cores. For example, siRNA can be encapsulated within the internal core of the bilayer vesicle and delivered in that manner. The prepared amphiphilic cyclodextrins are rehydrated by addition of a solution of the siRNA, allowing the siRNA to be encapsulated within the internal core of the bilayer vesicles or, in the case of the cationic cyclodextrins, within multilayered nanoparticles. The vesicles can also be used to transport lipophilic molecules, which would be encapsulated within the lipophilic layers of the vesicles.

Micelles formed from the derivatives of the present invention will have a hydrophilic exterior, as a result of the primary hydrophilic side of the derivatives facing outwards. The cores of the micelles will be occupied by the secondary side of the cyclodextrins, and thus will have both hydrophilic and lipophilic groups. As the lipophilic groups will be more dominant it is envisaged that the micelles will generally be used to deliver lipophilic molecules within their cores; there is a possibility however that hydrophilic molecules will also be delivered, by attachment to the hydrophilic groups on the secondary side.

The monolayers will have a hydrophilic side, provided by the primary side of the derivatives, and an overall lipophilic side provided by the secondary side of the derivatives. The monolayers could be attached to the surface of a stent for example, and a drug could also be complexed to the monolayer and thus delivered via the stent.

A typical molecule which could be delivered via a nanoparticle would be DNA. In this case a solution of DNA would be added and the cyclodextrin derivatives would form nanoparticles with the DNA. The invention also allows any nanoparticles formed to be modified or further modified after assembly. This is particularly useful if large molecules such as antibodies need to be attached. It has been found that if the antibody is attached to the derivative prior to assembly that this can lead to hydrophilic/lipophilic balancing problems, which may prevent self assembly in aqueous solvent. However, as the hydrophilic group on the primary side is available to be modified after assembly, this further elaborates the functionality of the assemblies.

It has also been found that the assemblies can complex to a number of different bulky lipophilic groups by hydrophobic inclusion of these groups into the cyclodextrin cavities. Examples of these groups are cholesteryl and adamantyl which when attached to non-lipophilic groups such as PEG may enable attachment of these latter groups to the assemblies. Cholesteryl is a polycyclic steroid and adamantane is a tricyclic molecule having having ten carbons ($C_{10}H_{16}$). This complex provides two major advantages, namely a number of different molecules can be attached to the assembly in this manner, either directly or via PEG linkages, as targeting functions, an example being an antibody or a protein such as transferrin. Additionally, PEG or modified PEG attached in this manner will reduce toxicity and increase circulation time of the administered assembly.

Various surface-coated assemblies may also be formed in different ways

One surface-coated assembly can be formed from the self-assembly in aqueous solvent of one or more of the macrocyclic derivatives of the invention coated with a further macrocyclic derivative of the invention. Ideally, the coating takes place by amphiphilic or electrostatic interaction.

A further surface-coated assembly can be formed from the self-assembly in aqueous solvent of one or more of the macrocyclic derivatives of the invention coated with a polyamine, peptide, protein, oligosaccharide, polysaccharide, antibody and/or antibody fragment. Ideally, the coating takes place by amphiphilic or electrostatic interaction.

A further surface-coated assembly can be formed from the self-assembly in aqueous solvent of one or more of the macrocyclic derivatives of the invention coated with a cholesterol, adamantane and/or other lipid derivative. Ideally, the coating takes place by host-guest inclusion.

A composition comprising a nucleic acid, nucleotide or nucleotide analogue $Nuc_n$ (n=1,2,3, . . . 50); and one or more macrocyclic derivatives or assemblies of the invention may also be formed. Such compositions may be used in the enhancement of the delivery of a nucleic acid, nucleotide or nucleotide analogue to cells, preferably mammalian cells.

Compositions comprising a nucleic acid, nucleotide or nucleotide analogue $Nuc_n$ (n=1,2,3, . . . 50); and one or more macrocyclic derivatives or assemblies of the invention can also be surface-coated in the ways listed above. Such surface-coated compositions may also be used in the enhancement of the delivery of a nucleic acid, nucleotide or nucleotide analogue to cells.

In this manner, the invention also provides methods for in-vitro transfer of a guest molecule into biological cells, comprising the treatment of a suspension of biological cells with a derivative or assembly of the invention wherein contact between the suspension of the biological cells and the derivative and/or assembly effects the transfer of the guest molecule into the biological cells. Ideally, the guest molecule is a nucleic acid, nucleotide or nucleotide analogue $Nuc_n$ (n=1,2, 3, . . . 50). Treatment essentially involves contacting the suspension with the derivative and/or assembly of the invention. Ideally, the treatment occurs for 1 to 72 hours.

The present invention will now be described with reference to the following examples:

Example 1 illustrates the modification of cyclodextrin by a reaction sequence which introduces lipophilic groups at the 2-position before hydrophilic groups are introduced at the 6-position.

Example 2 illustrates the modification of cyclodextrin by a reaction sequence which introduces hydrophilic groups at the 6-position before lipophilic groups are introduced at the 2-position.

Example 3 illustrates the formation of bilayer vesicles according to FIG. 1.

Figure 2:
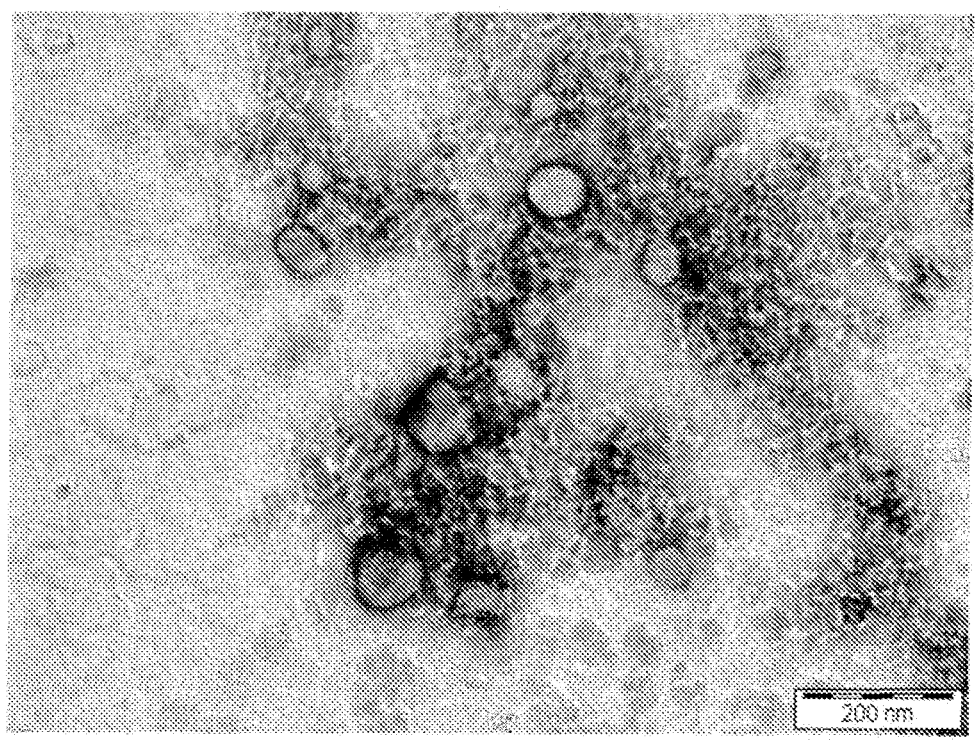
FIG. 2 shows the TEM results of the formation of nanoparticulate complexes of heptakis[6-(2'-aminoethylthio)-2-O-octyloxycarbonylethylsulfanyipropyl]-β-cyclodextrin trifluoroacetic acid salt with DNA according to Example 4.

Example 4 illustrates the formation of nanoparticles with DNA according to FIG. 2.

Figure 3:
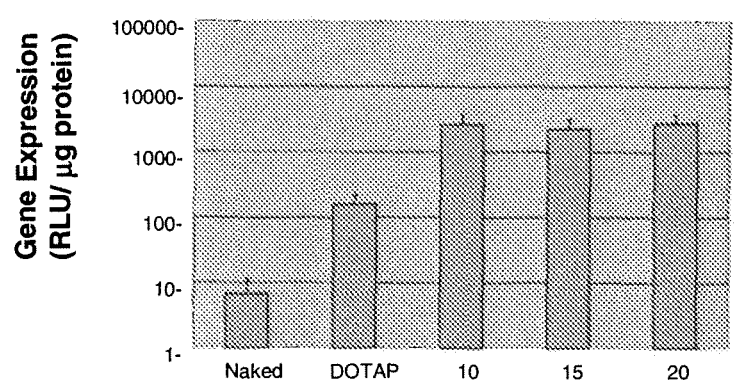
FIG. 3 shows the transfection of biological cells Cos-7 with heptakis[6-(2'-aminoethylthio)-2-O-octyloxycarbonylethylsulfanylpropyl]-β-cyclodextrin trifluoroacetic acid salt-DNA complex in comparison to DOTAP-DNA according to Example 5.

Example 5 illustrates the transfection of biological cells with heptakis[6-(2'-aminoethylthio)-2-O-octyloxycarbonyl-ethylsulfanylpropyl]-β-cyclodextrin trifluoroacetic acid salt according to FIG. 3.

EXAMPLES

General Experimental Procedures

Chemical Materials

All chemicals were purchased from the Aldrich chemical company and were used without further purification unless noted.

Triphenylphosphine was recrystallised from ethanol and dried under high vacuum for 6 hours at 50° C. prior to use.

β-cyclodextrin was dried for 12 hours at 100° C. under high vacuum prior to use.

DMF was purchased in Sureseal bottles over molecular sieves and stored under nitrogen.

Chromatography

TLC was performed on aluminium-backed plates of Merck Silica Kieselgel 60 $F_{254}$. Carbohydrate $R_f$ values were found by dipping the plates in a 5% sulfuric acid in ethanol solution and heating using a heatgun.

Cesium sulfate stain: (21 g $(NH_4)_6Mo_7O_{24}$, 1 g $Ce(SO_4)_2$, 1 L $H_2O$, 31 mL conc. $H_2SO_4$); TLC plates were dipped in this stain followed by charring to visualize some compounds.

Iodine tank: iodine was mixed with sand in a tank within which TLC plates were allowed stand for some visualisations.

Flash chromatography: this was carried out using Merck Kieselgel 60 0.04-0.063 mm.

NMR Spectroscopy $^1H$ NMR spectra were recorded using Varian 300 MHz, 400 MHz and 500 MHz spectrometers at 25° C. unless stated.

$^{13}C$ NMR spectra were recorded using Varian 75 MHz 100 MHz and 125 MHz spectrometers at 25° C. unless stated.

The atom-numbering scheme is indicated under Example 1 and other atoms listed in the NMR data are identified by the atomic groups in which they occur.

Mass Spectrometry

MALDI-TOF analyses were performed on a Perseptive (Framingham, Mass.) Voyager STR instrument equipped with delayed extraction technology. Ions were formed by a pulsed UV laser beam (nitrogen laser, i) 337 nm) and accelerated through 24 kV. Samples were diluted in $CHCl_3$ and mixed 1:1 v/v with the matrix solution obtained by dissolving 2,5-dihydroxybenzoic acid (DHB) in $CH_3OH$/0.1% trifluoroacetic acid/$CH_3CN$ (1:1:1 by volume) at a concentration of 30 mg/mL. Exactly 1/L of this mixture was deposited onto a stainless steel 100 sample MALDI plate and allowed to dry at room temperature before running the spectra in the positive polarity.

Example 1

The Modification of Cyclodextrin by a Reaction Sequence which Introduces Lipophilic Groups at the 2-position Before Hydrophilic Groups are Introduced at the 6-position a) Preparation of heptakis(6-O-tert-butyldimethylsilyl)-β-cyclodextrin

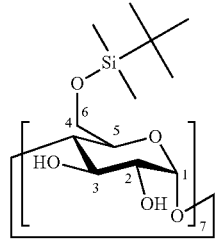

Dry β-cyclodextrin (14 g, 12.3 mmol) was dissolved slowly in anhydrous pyridine (250 mL) with constant stirring to avoid formation of a thick gel. The solution was cooled to 0° C. using an ice bath. A solution of tert-butyldimethylsilyl-chloride (16.8 g, 111.4 mmol) dissolved in anhydrous pyridine (50 mL) was added dropwise to the reaction vessel over a period of 30 minutes. The reaction mixture was stirred for a further 3 hours at 0° C. and then at room temperature for 24 hours under nitrogen. The progress of the reaction was monitored by TLC, using the solvent system $CHCl_3$:MeOH:$H_2O$ (50:10:1). ($R_f$ β-cyclodextrin=0, $R_f$ product=0.21). Upon completion, the reaction solution was poured into distilled water (300 mL) causing the product to precipitate out of solution. The product was filtered and dissolved in $CHCl_3$ (150 mL) and then washed with potassium hydrogensulfate (1.0 M, 200 mL) followed by brine (200 mL). The chloroform was evaporated under reduced pressure and the product then recrystallised from a mixture of MeOH:$CHCl_3$ (95:5). The product was dried under high vacuum at 45° C. for 12 hours to afford a white powder (Yield 16.2 g, 68%).

$^1H$ NMR (500 MHz, $CDCl_3$): δ 6.69 (br s, 7H, OH-2); 5.25 (br s, 7H, OH-3); 4.89 (d, J=3.4 Hz, 7H. H-1), 4.03 (t, J=9.2 Hz, 7H, H-3); 3.91 (dd, J=2.9 Hz, J=11.4 Hz, 7H, H-6$_b$); 3.71 (d, J=10.4 Hz, 7H, H-6$_a$), 3.65-3.62 (m, 14H, H-2, H-5); 3.56 (t, J=9.2 Hz, 7H, H-4); 0.87 (s, 63H, C(CH$_3$)$_3$); 0.04 (s, 21H, Si—CH$_3$); 0.03 (s, 21H, Si—CH$_3$).

$^{13}C$ NMR (125 MHz, $CDCl_3$): δ 102.2 (C-1); 81.9 (C-4); 73.8, 73.6 (C-2, C-3); 72.7 (C-5); 61.8 (C-6); 26.1 (C(CH$_3$)$_3$); 18.4 (SiC(CH$_3$)$_3$); −4.9, −5.1 (Si(CH$_3$)$_3$).

Elemental Analysis: $C_{84}H_{168}O_{35}Si_7$ Theory: C 52.14, H 8.75%, Found: C 51.76, H 8.58%.

b) Preparation of heptakis(2-O-allyl-6-O-tert-butyldimethylsilyl)-β-cyclodextrin

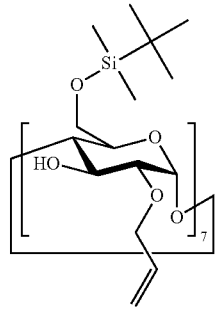

Heptakis(6-O-tert-butyldimethylsilyl)-β-cyclodextrin (5.09 g, 2.63 mmol) was dissolved in anhydrous DMF (240 mL) and cooled to 0° C. using an ice bath. Sodium hydride (0.5 g, 20.83 mmol) was added portion-wise and stirred for a further 1.5 hours at 0° C. followed by stirring at room temperature overnight under nitrogen. (Note: the reaction solution gradually foams upon stirring due to the sodium hydride but this subsides overnight). The reaction solution was again cooled to 0° C. and allyl bromide (1.64 mL, 18.95 mmol) was added dropwise and stirred for 1 hour at 0° C. The reaction solution was then allowed to warm slowly to room temperature and stirred overnight under nitrogen. Conversion of the starter to product was confirmed by TLC using the solvent system cyclohexane:ethyl acetate (4:1). ($R_f$ starter=0, $R_f$ product=0.34). The reaction solution was concentrated under reduced pressure and the resulting residue was taken up in $CH_2Cl_2$ (250 mL) and washed with brine (200 mL). The $CH_2Cl_2$ layer was then dried over magnesium sulfate, filtered and concentrated. The product heptakis(2-O-allyl-6-O-tert-butyldimethylsilyl)-β-cyclodextrin was purified by column chromatography on silica gel using cyclohexane:ethyl acetate (4:1) as eluent and isolated as a white foam (Yield 2.5 g, 44%).

$^1$H NMR (500 MHz, CDCl$_3$): δ 5.99-5.91 (m, 7H, C$\underline{H}$=CH$_2$); 5.3 (dd, J$_{gem}$=1.4 Hz, J$_{vic}$=17.2 Hz, 7H, CH=C$\underline{H}_2$trans); 5.2 (dd, J$_{gem}$=1 Hz, J$_{vic}$=10.4 Hz, 7H, CH=C$\underline{H}_2$cis); 4.89 (d, J=3.4 Hz, 7H, H-1); 4.88 (s, 7H, OH-3); 4.47 (dd, J=5.4 Hz, J=12.7 Hz, 7H, OCH$_b$); 4.22 (dd, J=6.9 Hz, J=12.6 Hz, 7H, OCH$_a$); 3.96 (t, J=9.2 Hz, 7H, H-3); 3.92 (dd, J=3.0 Hz, J=11.3 Hz, 7H, H-6$_b$); 3.65 (d, J=10.4 Hz, 7H, H-6$_a$); 3.57 (d, J=9.3 Hz, 7H, H-5); 3.49 (t, J=9.2 Hz, 7H, H-4); 3.31 (dd, J=3.6 Hz, J=9.6 Hz, H-2), 0.87 (s, 63H, C(CH$_3$)$_3$); 0.03 (s, 21H, SiCH$_3$), 0.02 (s, 21H, SiCH$_3$).

$^{13}$C NMR (125 MHz, CDCl$_3$): δ 134.6 (C$\underline{H}$=CH$_2$); 118.3 (C$\underline{H}_2$=CH); 101.3 (C-1); 73.4 (OCH$_2$); 82.3 (C-4); 79.7 (C-2); 73.42 (C-3); 73.39 (OCH$_2$); 71.84 (C-5); 61.9 (C-6); 26.1 (C(C$\underline{H}_3$)$_3$); 18.4 (C(CH$_3$)$_3$); −4.9 (SiCH$_3$); −5.1 (SiCH$_3$).

Elemental Analysis: $C_{105}H_{196}O_{35}Si_7$ Theory: C, 56.93, H 8.92%, Found: C 56.91, H 8.69%.

c) Preparation of heptakis(6-O-tert-butyldimethylsilyl-2-O-dodecylsulfanylpropyl)-β-cyclodextrin

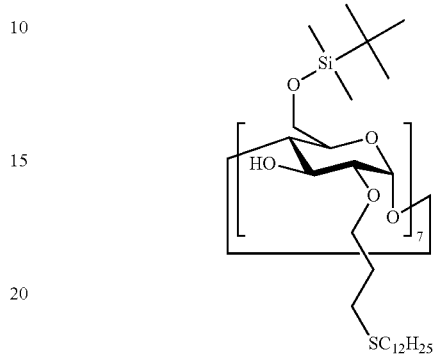

General procedure for photoaddition reactions: to a solution of the cyclodextrin heptakis(2-O-allyl-6-O-tert-butyldimethylsilyl)-β-cyclodextrin in cyclohexane (concentration of cyclodextrin derivative=5 mM) was added thiol (21 eq.) in a quartz glass tube. The solution was thoroughly degassed using ultrasound for 30 min and a stream of nitrogen was bubbled through the solution for 20 min. The solution, kept under an atmosphere of nitrogen, was irradiated with a low-pressure Hg lamp and stirred for 5 h. The completion of the reaction was checked by TLC, solvent system 15% ethyl acetate/cyclohexane or by $^1$H-NMR spectra. The solvent was removed under reduced pressure and the crude product was purified by column chromatography (SiO$_2$, EtOAc/cyclohexane from 0% to 10%) to afford the product as a colourless oil (from 60 to 95% yield). The residual solvent was removed by drying at 0.1 mm Hg at 40° C.

This compound was synthesised according to the general procedure from 210 mg (0.095 mmol) heptakis(2-O-allyl-6-O-tert-butyldimethylsilyl-)-β-cyclodextrin and 291.8 mg (2.0 mmol) 1-dodecylthiol using cyclohexane as the solvent (19 ml). Yield: 230 mg (74.8%) colourless oil.

$^1$H NMR (CDCl$_3$): δ=4.87 (7H, d, J=3, H-1); 4.86 (7H, s, OH-3); 3.98-4.06 (7H, m, H-3); 3.86-3.91 (14H, m, H-6); 3.67-3.76 (7H, m, H-2); 3.60-3.64 (7H, m, H-5); 3.51-3.54 (7H, m, H-4); 3.38-3.47 (AB, 7H, m, —CH$_2$—CH$_2$—O); 3.21 (AB, 7H, dd, J$_1$=3; J$_2$=8, CH$_2$—CH$_2$—O); 2.57 (14H, t, J=7, —O—CH$_2$—CH$_2$—CH$_2$—S); 2.48 (14H, t, J=7, —CH$_2$—CH$_2$—CH$_2$—CH$_2$—S); 1.81-1.92 (14H, m, —O—CH$_2$—CH$_2$—CH$_2$—S); 1.49-1.60 (14H, m, —CH$_2$—CH$_2$—CH$_2$—CH$_2$—S); 1.24 (126H, s, —(CH$_2$)$_9$—); 0.86 (21H, m, —CH$_3$); 0.85 (63H, s, SiC(CH$_3$)$_3$); 0.01 (21H, s, SiCH$_3$); 0.00 (21H, s, SiCH$_3$). Proton assignments were confirmed by COSY experiments.

$^{13}$C NMR (CDCl$_3$): δ=106.4 (C-1); 87.4 (C-4); 86.3 (C-5); 78.4 (C-3); 76.9 (C-2); 76.8 (OCH$_2$); 66.9 (C-6); 33.8-37.3 (—CH$_2$—); 31.1 (SiC(CH$_3$)$_3$); 27.9 (—CH$_2$—CH$_2$—S); 23.5 (SiC(CH$_3$)$_3$); 19.3 (—CH$_2$—CH$_2$—S); 0.2 (SiCH$_3$); 0.0 (SiCH$_3$).

Elemental analysis: $C_{189}H_{378}O_{35}S_7Si_7$ Theory: C, 62.50; H, 10.49; S, 6.18%, Found: C, 62.43; H, 10.60; S, 6.21%.

MS: $C_{189}H_{378}O_{35}S_7Si_7$ (3632.15).

d) Preparation of heptakis[6-bromo-2-O-(dodecylsulfanylpropyl)]-β-cyclodextrin

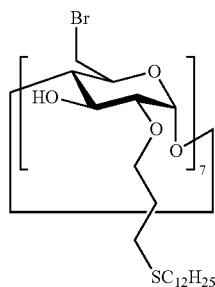

General procedure for preparation of 6-perbromo cyclodextrin derivatives: $Ph_3P:Br_2$ was freshly prepared by careful addition of $Br_2$ to $Ph_3P$ dissolved in $CH_2Cl_2$ maintained on an ice bath. When the reaction mixture was warmed to RT, a white suspension was formed. The 6-silylated cyclodextrin was then added to this suspension, and reaction mixture was stirred for 24 h at RT, during which time the suspension cleared. The dichloromethane solution was then washed with saturated aqueous $NaHCO_3$ solution, followed by brine. The $CH_2Cl_2$ layer was recovered and concentrated under reduced pressure to yield a product as an oil.

This compound was synthesised according to the general procedure from heptakis[6-O-tert-butyldimethylsilyl-2-O-dodecylsulfanylpropyl]-β-cyclodextrin 230 mg (0.017 mmol) and $Ph_3P:Br_2$ (freshly prepared by addition of 0.08 ml (1.5 mmol) $Br_2$ to 671 mg 1.6 mmol) $Ph_3P$) in 6 mL $CH_2Cl_2$. The dichloromethane solution was then washed with saturated aqueous $NaHCO_3$ solution, followed by brine. The $CH_2Cl_2$ layer was recovered and concentrated under reduced pressure to yield product as an oil. Column chromatography ($SiO_2$, 10% $MeOH/CH_2Cl_2$) afforded the product heptakis[6-bromo-2-O-(dodecylthiol-3-propyl)]-β-cyclodextrin 120 mg, (51% yield) as oil.

$^1H$ NMR ($CDCl_3$): δ=4.96 (7H, d, H-1); 4.9 (7H, s, OH-3); 4.09-4.0 (7H, m, H-3); 3.9-3.6 (m, H-2; H-5; H-4; H-5; —$CH_2$—$CH_2$—O; 42 H); 3.2-3.4 (m, 14 H; —$CH_2Br$ (H-6); 2.57 (14H, t, —O—$CH_2$—$CH_2$—$CH_2$—S); 2.48 (14H, t, —$CH_2$—$CH_2$—$CH_2$—S); 1.81-1.92 (14H, m, —O—$CH_2$—$CH_2$—$CH_2$—S); 1.49-1.60 (14H, m, —$CH_2$—$CH_2$—$CH_2$—$CH_2$—S); 1.23 (126H, s, —$(CH_2)_9$—); 0.85 (21H, m, —$CH_3$).

e) Preparation of heptakis[6-(2′aminoethylthio)-2-O-(dodecylsulfanylpropyl)]-β-cyclodextrin hepta-N-tBoc derivative

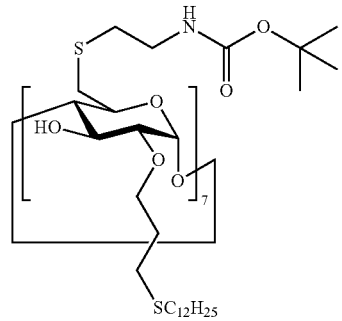

General procedure for introduction of 6-amino groups: 6-bromo cyclodextrins were treated with an excess of N-(tert-butyloxycarbonyl)-1,3-propanediamine (10 molar equiv amine per Br equivalent) at 80° C. for 24 h in DMF. The solvent was removed under vacuum, and residue was dissolved in $CH_2Cl_2$. The dichloromethane solution was then washed with 2 M HCl, followed by brine. After column chromatography ($SiO_2$, 20% $MeOH/CH_2Cl_2$) the product was afforded as a light brown oil.

This compound was synthesised according to the general procedure from heptakis[6-bromo-2-O-dodecylsulfanylpropyl]-β-cyclodextrin 120 mg (0.037 mmol) and 453 mg (2.6 mmol) N-(tert-butoxycarbonyl)-1,3-propanediamine (10 molar equiv. amine per Br equivalent) in 1 mL of DMF. Column chromatography ($SiO_2$, 20% $MeOH/CH_2Cl_2$) afforded the product heptakis[6-N-(tert-Butoxycarbonyl)-1,3-propanediamine-2-O-(dodecylthiol-3-propyl)]-β-cyclodextrin, 50 mg, (34% yield) as a viscous oil.

$^1H$ NMR ($CDCl_3$): δ=5.6 (br s 7H, NH) 5.37 (br s 7H, NH); 4.9-4.6 (14 H, m br, H-1; OH-3); 4.2-3.6 (br m, H-3; H-2; H-5; H-4; H-5; —$CH_2$—$CH_2$—O; 42 H); 3.2 (br m, 14 H Boc-NH$CH_2$—); 2.7 (br m 14 H NH$CH_2CH_2$—); 2.5 (14H, br m, —O—$CH_2$—$CH_2$—$CH_2$—S); 2.4 (14H, br m —$CH_2$—$CH_2$—$CH_2$—$CH_2$—S); 1.8-1.9 (14H, m, —O—$CH_2$—$CH_2$—$CH_2$—S); 1.7 (br m, 14 H, —$CH_2$—$CH_2$—$CH_2$); 1.6 (14H, m, —$CH_2$—$CH_2$—$CH_2$—$CH_2$—S); 1.36 (br s, 63H, $CH_3$/t-But) 1.21 (126H, s, —$(CH_2)_9$—); 0.81 (21H, m, —$CH_3$).

f) Preparation of heptakis[6-(2′aminoethylthio)-2-O-(dodecylsulfanylpropyl)]-β-cyclodextrin trifluoroacetic acid salt

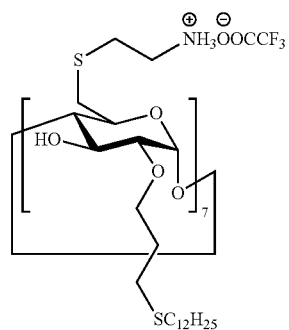

Heptakis[6-(2'aminoethylthio)-2-O-(dodecylsulfanylpropyl)]-β-cyclodextrin hepta-N-tBoc derivative (50 mg, 0.013 mmol) was dissolved in 2 ml CH$_2$Cl$_2$ and 0.33 ml TFA was added. Reaction mixture was stirred at rt for 12H. The TFA was then removed under reduced pressure. The product was obtained as the TFA-salt in near quantitative yield (60 mg).

$^1$H NMR (CDCl$_3$): δ=7.9 (br s~35 H, NH); 4.1-3.6 (m br, H-1; OH-3, H-3; H-2; H-5; H-4; H-5; —CH$_2$—CH$_2$—O; 42 H); 3.4-2.6 (br m 28 H NHCH$_2$CH$_2$—); 2.5 (14H, br m, —O—CH$_2$—CH$_2$—CH$_2$—S); 2.4 (14H, br m —CH$_2$—CH$_2$—CH$_2$—CH$_2$—S); 1.8-1.9 (14H, m, —O—CH$_2$—CH$_2$—CH$_2$—S); 1.7 (br m, 28 H, —CH$_2$—CH$_2$—CH$_2$); —CH$_2$—CH$_2$—CH$_2$—CH$_2$—S); 1.19 (126H, s, —(CH$_2$)$_9$—); 0.8 (21H, m, —CH$_3$).

Example 2

The Modification of Cyclodextrin by a Reaction Sequence which Introduces Hydrophilic Froups at the 6-position Before Lipophilic Groups are Introduced at the 2-position The following figure shows the structures of derivatives which may be made using the synthetic procedures outlined below.

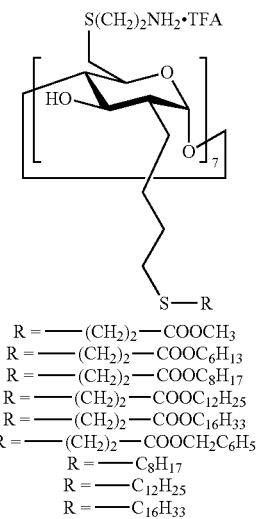

R = ——(CH$_2$)$_2$—COOCH$_3$
R = ——(CH$_2$)$_2$—COOC$_6$H$_{13}$
R = ——(CH$_2$)$_2$—COOC$_8$H$_{17}$
R = ——(CH$_2$)$_2$—COOC$_{12}$H$_{25}$
R = ——(CH$_2$)$_2$—COOC$_{16}$H$_{33}$
R = ——(CH$_2$)$_2$—COOCH$_2$C$_6$H$_5$
R = ——C$_8$H$_{17}$
R = ——C$_{12}$H$_{25}$
R = ——C$_{16}$H$_{33}$ a) Preparation of heptakis(2-O-allyl-6-bromo-6-deoxy)-β-cyclodextrin

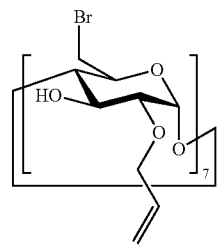

Triphenylphosphine (1.74 g, 6.63 mmol) was dissolved in freshly distilled CH$_2$Cl$_2$ (50 mL) and cooled to 0° C. Bromine (0.34 mL, 6.54 mmol) was added dropwise to the solution with stirring. Any remaining red colouration was dispelled by addition of more triphenylphosphine. The solution was allowed to warm slowly to room temperature during which time a fine white precipitate formed. Heptakis(2-O-allyl-6-O-tert-butyldimethylsilyl)-β-cyclodextrin (1.94 g, 0.876 mmol) was dissolved in freshly distilled CH$_2$Cl$_2$ (10 mL) and added dropwise to the triphenylphosphine solution. The reaction mixture was stirred for 24 hours under nitrogen at room temperature. Completion of the reaction was confirmed by TLC, cyclohexane:ethyl acetate (1:1). (R$_f$ starter=0.83, R$_f$ product=0.6). The CH$_2$Cl$_2$ was removed under reduced pressure to yield an oily residue. This residue was then triturated with EtOH (60 mL) and sonicated for 1 hour causing the product to precipitate out of solution. The precipitate was filtered and sonicated twice more with EtOH (2×60 mL). The precipitate was dried under high vacuum at 40° C. for 12 hours yielding the product as a white solid (Yield 1.2 g, 74%).

$^1$H NMR (500 MHz, CDCl$_3$): δ 5.97-5.89 (m, 7H, C$\underline{H}$=CH$_2$); 5.32 (dd, J$_{gem}$=1.3 Hz, J$_{vic}$=17.1 Hz, 7H CH=C$\underline{H}_2$trans); 5.25 (d, J=10.4 Hz, 7H, CH=C$\underline{H}_2$cis) 4.97 (d, J=3.6 Hz, 7H, H-1); 4.94 (s, 7H, OH-3), 4.48 (dd, J=5.2 Hz, J=12.4 Hz, 7H, OCH$_b$); 4.24 (dd, J=7 Hz, J=12.4 Hz, 7H, OCH$_a$); 3.96 (t, J=9.2 Hz, 7H, H-3); 3.86-3.81 (m, 14H, H-5, H-6$_b$); 3.70 (dd, J=6.1 Hz, J=11.5 Hz, 7H, H-6$_a$); 3.45 (dd, J=3.6 Hz, J=9.6 Hz, 7H, H-2); 3.33 (t, J=9.2 Hz, 7H, H-4).

$^{13}$C NMR (125 MHz, CDCl$_3$): δ 133.9 (CH=CH$_2$); 119.2 (CH$_2$=CH); 101.9 (C-1); 86.2 (C-4); 78.9 (C-2); 73.7 (OCH$_2$); 73.0 (C-3); 70.7 (C-5), 33.3 (C-6).

Elemental Analysis: C$_{63}$H$_{91}$O$_{28}$Br$_7$ Theory: C 40.78, H 4.94, Br 30.14%, Found: C 40.58, H 4.73, Br 30.42%.

b) Preparation of heptakis[2-O-allyl-6-(2'-aminoethylthio)]-β-cyclodextrin hepta-N-tBoc derivative

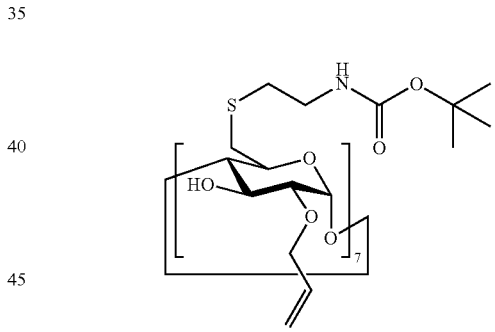

N-(2-Mercaptoethyl)-carbamic acid tert-butyl ester (1.43 g, 8.085 mmol) was dissolved in anhydrous DMF (10 mL) and sodium hydride (0.19 g, 7.546 mmol) was added portionwise carefully with gentle stirring. This solution was stirred for a further 10 minutes under nitrogen and then for 20 minutes at 80° C. before allowing to cool slowly back to room temperature. Heptakis(2-O-allyl-6-bromo-6-deoxy)-β-cyclodextrin (1.0 g, 0.539 mmol) was dissolved in anhydrous DMF (5 mL) and added dropwise to the reaction vessel and the solution was then stirred for 18 hours under a nitrogen atmosphere. TLC analysis indicated that the reaction had gone to completion; the solvent system used was ethyl acetate:cyclohexane (6:4). (R$_f$ starter=0.8, R$_f$ product=0.65). The reaction mixture was concentrated under reduced pressure to yield an oily residue which was taken up in ethyl acetate (30 mL) and washed with deionised water (40 mL) followed by brine (40 mL). The organic layer was then dried over MgSO$_4$, filtered and the ethyl acetate evaporated off. The crude residue was purified by column chromatography on silica gel using cyclohexane:ethyl acetate (1:1, $R_f$ product=0.29) as eluent yielding a creamy powder as product (Yield 1.0 g, 74%).

$^1$H NMR (500 MHz, CDCl$_3$): δ 5.97-5.89 (m, 7H, C<u>H</u>═CH$_2$); 5.32-5.21 (m, 21H, C<u>H</u>$_2$═CH, NH); 4.96-4.92 (m, 14H, OH-3, H-1); 4.47 (dd, J=5.3 Hz, J=12.5 Hz, 7H, OCH$_b$); 4.23 (dd, J=6.9 Hz, J=12.4 Hz, 7H, OCH$_a$); 3.91-3.87 (m, 14H, H-3, H-5); 3.41-3.39 (m, 14H, H-4, H-2); 3.3 (br s, 7H, NCH$_2$); 3.05-2.87 (m, 14H, H-6$_b$, H-6$_a$); 2.73 (br s, 14H, SCH$_2$); 1.43 (s, 63H, C(CH$_3$)$_3$).

$^{13}$C NMR (125 MHz, CDCl$_3$): δ 156.0 (C═O); 134.2 (<u>C</u>H═CH$_2$); 118.9 (<u>C</u>H$_2$═CH); 101.8 (C-1); 86.2 (C-4), 79.3 (C-2, <u>C</u>(CH$_3$)$_3$); 73.6 (OCH$_2$); 73.3 (C-3); 71.0 (C-5); 40.2 (CH$_2$N); 33.7 (SCH$_2$, C-6); 28.7 (C(<u>C</u>H$_3$)$_3$).

Elemental Analysis: C$_{112}$H$_{189}$O$_{42}$N$_7$S$_7$ Theory: C 53.17, H 7.53, N 3.88, S 8.87%, Found: C 52.98, H 7.46, N 3.74, S 9.17%.

c) Preparation of heptakis[6-(2'-aminoethylthio)-2-O-octyloxycarbonylethylsulfanylpropyl]-β-cyclodextrin hepta-N-tBoc derivative

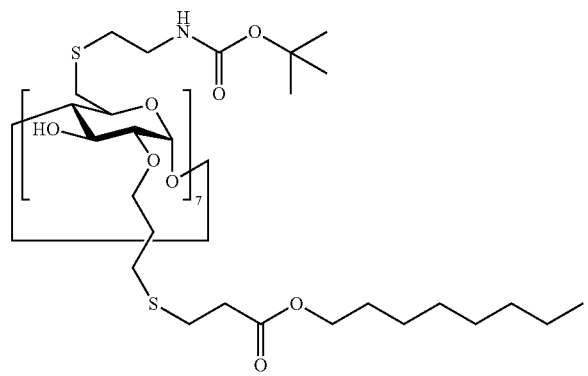

Heptakis[2-O-allyl-6-(2'-aminoethylthio)]-β-cyclodextrin hepta-N-t-Boc derivative (0.32 g, 0.127 mmol) was dissolved in MeOH (25 mL) in a quartz test-tube using gentle heating and stirring to effect dissolution. Octyl-3-mercaptopropionate (0.58 g, 2.67 mmol) and AIBN (10 mg, 0.0635 mmol) were both then added to the reaction vessel. The reaction solution was degassed by bubbling nitrogen through the solution for a period of 30 minutes after which time the vessel was sealed under an atmosphere of nitrogen. The quartz vessel was clamped in front of a UV lamp and irradiated with ultra violet light (254 nm) for a period of 19 hours. After this period a sample (1 mL) was taken from the reaction, evaporated to dryness and submitted for $^1$H NMR analysis. Disappearance of the multiplet from δ 5.97-5.89 indicated that full photoaddition had occurred and the reaction had reached completion. The reaction solution was concentrated under reduced pressure and the crude residue was purified by column chromatography on silica gel using a gradient solvent system of cyclohexane:ethyl acetate (6.5:3.5 to 1:1). The product was isolated as a colourless resin (0.45 g, 86%).

$^1$H NMR (500 MHz, CDCl$_3$): δ 5.31 (br s, 7H, NH); 4.92 (br s, 14H, OH-3, H-1); 4.08-4.02 (m, 21H, CO$_2$CH$_2$, OCH$_b$); 3.85-3.82 (m, 14H, H-3, H-5); 3.77-3.73 (m, 7H, OCH$_a$); 3.38-3.31 (m, 28H, H-4, H-2, CH$_2$N); 3.05-2.87 (m, 14H, H-6$_b$, H-6$_a$); 2.78-2.73 (m, 28H, CH$_2$CO$_2$, SCH$_2$CH$_2$N); 2.63-2.57 (m, 28H, C<u>H</u>$_2$SC<u>H</u>$_2$CH$_2$CO$_2$); 1.90-1.84 (m, 14H, OCH$_2$C<u>H</u>$_2$); 1.64-1.58 (m, CO$_2$CH$_2$C<u>H</u>$_2$); 1.43 (s, 63H, C(CH$_3$)$_3$); 1.34-1.24 (m, 70H, CH$_2$×5); 0.87 (t, J=6.9 Hz, 21H, CH$_2$C<u>H</u>$_3$).

$^{13}$C NMR (125 MHz, CDCl$_3$): δ 172.1 (CH$_2$<u>C</u>═O); 156.0 (NC═O); 101.7 (C-1); 86.1 (C-4); 80.9 (C-2); 79.3 (<u>C</u>(CH$_3$)$_3$); 73.1 (C-3); 71.8 (OCH$_2$); 71.1 (C-5); 65.0 (CO$_2$<u>C</u>H$_2$); 40.2 (CH$_2$N); 35.0 (S<u>C</u>H$_2$CH$_2$CO$_2$); 33.6 (C-6, S<u>C</u>H$_2$CH$_2$N); 31.9, 29.32, 29.29, 26.0, 22.8 (CH$_2$×5); 29.8 (OCH$_2$<u>C</u>H$_2$); 28.74, 28.64, 28.59 (C(<u>C</u>H$_3$)$_3$, OCH$_2$CH$_2$CH$_2$, CO$_2$CH$_2$<u>C</u>H$_2$); 27.1 (<u>C</u>H$_2$CO$_2$); 14.2 (CH$_2$<u>C</u>H$_3$).

Elemental Analysis: C$_{189}$H$_{343}$O$_{56}$N$_7$S$_{14}$ Theory: C 55.93, H 8.52, N 2.42, S 11.06%, Found: C 55.72, H 8.44, N 2.21, S 10.79%.

d) Preparation of heptakis[6-(2'-aminoethylthio)-2-O-octyloxycarbonylethylsulfanylpropyl]-β-cyclodextrin trifluoroacetic acid salt

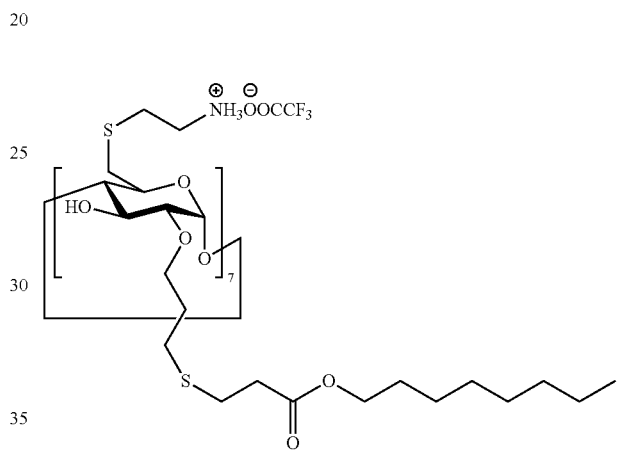

Heptakis[6-(2'-aminoethylthio)-2-O-octyloxycarbonylethylsulfanylpropyl]-β-cyclodextrin hepta-N-t-Boc derivative (0.22 g, 0.054 mmol) was dissolved in CH$_2$Cl$_2$ (5 mL) and TFA (0.2 mL, 2.7 mmol) was added with stirring. The reaction mixture was stirred for 24 hours at room temperature under nitrogen. After this period the reaction solution was concentrated and purified by size exclusion chromatography on LH20-100 Sephadex using MeOH as eluent. The product was dried on a high-vacuum pump for 8 hours and was isolated as a colourless solid (0.18 g, 89%).

$^1$H NMR (500 MHz, CD$_3$OD): δ 5.08 (d, J=3.5 Hz, 7H, H-1); 4.13-4.05 (m, 21H, CO$_2$CH$_2$, OCH$_b$); 3.93-3.80 (m, 21H, H-3, H-5, OCH$_b$); 3.55 (t, J=9.1 Hz, 7H, H-4); 3.44 (dd, J=3.5 Hz, J=9.6 Hz, 7H, H-2); 3.21 (t, J=7.1 Hz, 14H, CH$_2$N); 3.12 (d, J=12.9 Hz, 7H, H-6$_b$); 3.03-2.92 (m, 21H, SC<u>H</u>$_2$CH$_2$N, H-6$_a$); 2.81 (t, J=14.3 Hz, CH$_2$CO$_2$); 2.74-2.63 (m, 28H, C<u>H</u>$_2$SC<u>H</u>$_2$CH$_2$CO$_2$); 1.92-1.86 (m, 14H, OCH$_2$C<u>H</u>$_2$); 1.69-1.64 (m, 14H, CO$_2$CH$_2$C<u>H</u>$_2$); 1.41-1.32 (m, 56H, CH$_2$×5); 0.92 (t, J=7.0 Hz, 21H, CH$_3$).

$^{13}$C NMR (125 MHz, CD$_3$OD): δ 173.7 (CH$_2$<u>C</u>═O); 163.1 (F$_3$C<u>C</u>═O); 118.2 (CF$_3$); 102.7 (C-1); 87.0 (C-4); 82.0 (C-2); 74.3 (C-3); 73.5 (C-5); 72.7 (OCH$_2$); 65.9 (CO$_2$CH$_2$); 40.0 (CH$_2$N); 36.1 (S<u>C</u>H$_2$CH$_2$CO$_2$); 33.8 (C-6); 33.0, 30.4, 30.3, 27.1, 23.8 (CH$_2$×5); 31.7 (S<u>C</u>H$_2$CH$_2$N); 31.3 (OCH$_2$<u>C</u>H$_2$); 29.8 (CO$_2$CH$_2$<u>C</u>H$_2$); 29.3 (OCH$_2$CH$_2$<u>C</u>H$_2$); 28.0 (<u>C</u>H$_2$CO$_2$); 14.7 (CH$_3$).

Mass Spectrometry: TOF MS ES+ m/z 1680.2 [M+H]$^{2+}$; 3360.5 [M+2H]$^+$; C$_{154}$H$_{287}$O$_{42}$N$_7$S$_{14}$.

Example 2a

The Modification of Cyclodextrin by a Reaction Sequence which Introduces Hydrophilic Groups at the 6-position Before Lipophilic Groups are Introduced at the 2-position—additional compounds synthesised by the method of Example 2

Synthesis of 3-mercaptopropionic acid esters

General Procedure:

To mercaptopropionic acid (20 mmol) in solution in the appropriate alcohol (60 mmol) was added two drops of concentrated sulphuric acid. The reaction solution was stirred overnight at room temperature, then diluted with $CH_2Cl_2$ and washed with distilled water. The organic layer was dried ($MgSO_4$) and evaporated, and the residue was purified by column chromatography on silica gel.

Hexyl 3-mercaptopropionate

Column chromatography (cyclohexane-ethyl acetate 90:10) gave 5.6 g, 63% (Found: C, 56.88; H, 9.44; S, 16.76. $C_9H_{18}O_2S$ requires C, 56.80; H, 9.53; S, 16.85%). $\delta_H$ (300 MHz, $CDCl_3$) 4.10 (t, J=6.7 Hz, $CO_2CH_2$), 2.82-2.74 (m, 2H, $CH_2SH$), 2.67-2.62 (m, 2H, $CH_2CO_2$), 1.66-1.58 (m, 3H, $CO_2CH_2CH_2$, SH), 1.37-1.27 (m, 6H, $CH_2\times3$), 0.89 (t, J=6.8 Hz, 3H, $CH_3$); $\delta_C$ (75 MHz, $CDCl_3$) 171.8 (C=O), 65.1 ($CO_2CH_2$), 31.6, 28.7, 25.7, 22.7 ($CH_2\times4$), 20.0 ($CH_2SH$), 14.1 ($CH_3$).

Octyl 3-mercaptopropionate

Column chromatography ($CH_2Cl_2$) gave 2.50 g, 61% (Found C, 60.32; H, 10.03; S, 14.44. $C_{11}H_{22}O_2S$ requires C, 60.50; H, 10.15; S, 14.68%). $\delta_H$ (300 MHz, $CDCl_3$) 4.08 (t, J=6.7 Hz, 2H, $CO_2CH_2$), 2.80-2.72 (m, 2H, $CH_2SH$), 2.65-2.6 (m, 2H, $CH_2CO_2$), 1.64-1.57 (m, 3H, SH, $CO_2CH_2CH_2$), 1.35-1.26 (m, 10H, $CH_2\times5$), 0.86 (t, J=6.7 Hz, 3H, $CH_3$); $\delta_C$ (75 MHz, $CDCl_3$) 171.8 (C=O); 65.0 ($CO_2CH_2$); 38.7 ($CH_2CO_2$); 31.9, 29.30, 29.28, 28.7, 26.0, 22.7 ($CH_2\times6$); 19.9 ($CH_2SH$); 14.2 ($CH_3$).

Dodecyl 3-mercaptopropionate

The dodecyl ester (3.74 g, 73%) was obtained as colourless oil (Found C, 60.32; H, 10.03; S 14.44. $C_{15}H_{30}O_2S$ requires C, 60.51; H, 10.16; S, 14.68%). $\delta_H$(300 MHz, $CDCl_3$) 4.05 (t, J=6.7 Hz, 2H, $CO_2CH_2$), 2.76-2.69 (m, 2H, $CH_2SH$), 2.62-2.57 (m, 2H, $CH_2CO_2$), 1.62-1.56 (m, 3H, SH, $CO_2CH_2CH_2$), 1.26-1.22 (m, 18H, $CH_2\times9$), 0.84 (t, J=6.7 Hz, 3H, $CH_3$); $\delta_C$ (75 MHz, $CDCl_3$) 171.6 (C=O), 64.9 ($CO_2CH_2$), 38.6 ($CH_2CO_2$), 32.0-22.7 (alkyl chain), 19.8 ($CH_2SH$), 14.1 ($CH_3$).

Hexadecyl 3-mercaptopropionate

This reaction was performed at 50° C. Column chromatography ($CH_2Cl_2$) gave 4.62 g, 74% (Found C, 69.33; H, 11.32; S, 10.08. $C_{19}H_{38}O_2S$ requires C, 69.03; H, 11.59; S, 9.70%). $\delta_H$ (400 MHz, $CDCl_3$) 4.09 (t, J=6.75 Hz, $CO_2CH_2$), 2.79-2.73 (m, 2H, $CH_2SH$), 2.65-2.61 (m, 2H, $CH_2CO_2$), 1.65-1.58 (m, 3H, SH, $CO_2CH_2CH_2$), 1.35-1.24 (m, 26H, $CH_2\times13$), 0.87 (t, J=6.7 Hz, 3H, $CH_3$); $\delta_C$ (100 MHz, $CDCl_3$) 171.8 (C=O), 65.0 ($CO_2CH_2$), 38.7 ($CH_2CO_2$), 32.1-22.8 (alkyl chain), 19.9 ($CH_2SH$), 14.2 ($CH_3$).

Benzyl 3-mrcaptopropionate

Column chromatography (cyclohexane-ethyl acetate 90:10) gave 0.75 g, 54% (Found C, 61.25; H, 6.14; S, 15.93. $C_{10}H_{12}O_2S$ requires C, 61.20; H, 6.16; S, 16.34%). $\delta_H$ (400 MHz, $CDCl_3$) 7.38-7.33 (m, 5H, $C_6H_5$), 5.16 (s, 2H, $CH_2C_6H_5$), 2.83-2.77 (m, 2H, $CH_2SH$), 2.72-2.69 (m, 2H, $CH_2CO_2$), 1.64 (t, J=8.2 Hz, 1H, SH); $\delta_C$ (100 MHz, $CDCl_3$) 171.5 (C=O), 135.8 ($OCH_2CPh$), 128.7, 128.5, 128.4 (Ph), 66.6 ($CH_2Ph$), 38.6 ($CH_2CO_2$), 19.9 ($CH_2SH$).

Heptakis[6-(N-Boc-2-amino-ethylthio)-6-deoxy-2-O-methoxycarbonylethylsulfanylpropyl]-β-cyclodextrin Heptakis [2-O-allyl-6-(N-Boc-2-aminoethylthio)-6-deoxy]-β-cyclodextrin (0.37 g, 0.15 mmol) was dissolved in MeOH (30 mL) using gentle heat in a quartz test-tube. Methyl-3-mercaptopropionate (0.33 mL, 3.1 mmol) and AIBN (0.012 g, 0.1 mmol) were added and the reaction solution was degassed for 30 min with nitrogen. The reaction solution was irradiated (λ=254 nm) for 6 h, then concentrated and the residue purified by column chromatography ($SiO_2$, ethyl acetate-cyclohexane 60:40) to afford product (0.4 g, 82%) as a colourless resin (Found C, 49.74; H, 7.22; N, 3.10; S, 13.04. $C_{140}H_{245}O_{56}N_7S_{14}$ requires C, 49.88; H, 7.33; N, 2.91; S, 13.32%). $\delta_H$ (500 MHz, $CDCl_3$) 5.30 (br s, 7H, NH), 4.92 (br s, 14H, H-1, OH-3), 4.06-4.01 (m, 7H, $OCH_b$), 3.86-3.82 (m, 14H, H-3, H-5), 3.77-3.73 (m, 7H, $OCH_b$), 3.69 (s, 21H, $CO_2CH_3$), 3.39-3.30 (m, 28H, H-4, H-2, $CH_2N$), 3.06-2.89 (m, 14H, H-$6_b$, H-$6_a$), 2.79-2.73 (m, 28H, $CH_2CO_2$, $SCH_2$), 2.63-2.59 (m, 28H, $SCH_2CH_2CO_2$, $OCH_2CH_2CH_2$), 1.89-1.84 (m, 14H, $OCH_2CH_2$), 1.43 (s, 63H, $C(CH_3)_3$); $\delta_C$ (125 MHz, $CDCl_3$) 172.4 ($CH_2C$=O), 155.9 (NC=O), 101.6 (C-1), 86.0 (C-4), 80.8 (C-2), 79.3 ($C(CH_3)_3$), 73.0 (C-3); 71.7 ($OCH_2$), 71.1 (C-5), 51.8 ($CO_2CH_3$), 40.1 ($CH_2N$), 34.7 ($SCH_2CH_2CO_2$), 33.5 ($SCH_2CH_2N$, C-6), 29.7 ($OCH_2CH_2$), 28.6 ($C(CH_3)_3$), 28.5 ($OCH_2CH_2CH_2$), 26.9 ($CH_2CO_2$).

Heptakis[6-(N-Boc-2-amino-ethylthio)-6-deoxy-2-O-hexyloxycarbonylethylsulfanylpropyl]-β-cyclodextrin This compound was prepared from heptakis [2-O-allyl-6-(N-Boc-2-aminoethylthio)-6-deoxy]-β-cyclodextrin (0.4 g, 0.15 mmol) and hexyl-3-mercaptopropionate (0.63 g, 3.3 mmol). Irradiation for 24 h, then column chromatography ($SiO_2$, cyclohexane-ethyl acetate 60:40) afforded product (0.45 g, 74%) as a colourless resin (Found C, 52.23; H, 7.75; N, 2.49; S, 11.52. $C_{175}H_{315}O_{56}N_7S_{14}.8H_2O$ requires C, 52.46; H, 8.33; N, 2.45; S, 11.18%). $\delta_H$ (500 MHz, $CDCl_3$) 5.30 (br s, 7H, NH), 4.91 (br s, 14H, OH-3, H-1), 4.08-4.01 (m, 21H, $CO_2CH_2$, $OCH_b$), 3.85-3.81 (m, 14H, H-3, H-5), 3.76-3.72 (m, 7H, $OCH_a$), 3.38-3.30 (m, 28H, H-4, H-2, $CH_2N$), 3.04-2.86 (m, 14H, H-$6_b$, H-$6_a$), 2.77-2.71 (m, 28H, $CH_2CO_2$, $SCH_2CH_2N$), 2.62-2.06 (m, 28H, $OCH_2CH_2CH_2$, $SCH_2CH_2CO_2$), 1.89-1.83 (m, 14H, $OCH_2CH_2$), 1.63-1.58 (m, 14H, $CO_2CH_2CH_2$), 1.42 (s, 63H, $C(CH_3)_3$), 1.40-1.25 (m, 42H, $CH_2\times3$), 0.87 (t, J=6.8 Hz, 21H, $CH_2CH_3$); $\delta_C$ (125 MHz, $CDCl_3$) 172.0 ($CH_2C$=O), 155.9 (NC=O), 101.6 (C-1), 86.1 (C-4), 80.9 (C-2), 79.3 ($C(CH_3)_3$), 73.0 (C-3), 71.7 ($OCH_2$), 71.1 (C-5); 64.9 ($CO_2CH_2$), 40.1 ($CH_2N$); 35.0 ($SCH_2CH_2CO_2$), 33.6 ($SCH_2CH_2N$, C-6), 31.5, 25.6, 22.6 ($CH_2\times3$), 29.7 ($OCH_2CH_2$), 28.64, 28.59, 28.54 ($C(CH_3)_3$, $CO_2CH_2CH_2$, $OCH_2CH_2CH_2$), 27.0 ($CH_2CO_2$), 14.1 ($CH_2CH_3$).

Heptakis[6-(N-Boc-2-amino-ethylthio)-6-deoxy-2-O-dodecyloxycarbonylethylsulfanylpropyl]-β-cyclodextrin This compound was prepared from heptakis [2-O-allyl-6-(N-Boc-2-aminoethylthio)-6-deoxy]-β-cyclodextrin (0.15 g, 0.05 mmol) and dodecyl-3-mercaptopropionate (0.34 g, 1.2 mmol). The reaction solution was irradiated for 24 h after which an oily resin had separated. Column chromatography (SiO$_2$, cyclohexane-ethyl acetate 60:40) afforded product (0.17 g, 65%) as a colourless resin (Found C, 58.26; H, 8.95; N, 1.92. C$_{217}$H$_{399}$O$_{56}$N$_7$S$_{14}$ requires C, 58.55; H, 9.03; N, 2.20%). $\delta_H$ (400 MHz, CDCl$_3$) 5.31 (br s, 7H, NH), 4.92 (br s, 14H, H-1, OH-3), 4.09-4.02 (m, 21H, CO$_2$CH$_2$, OCH$_b$), 3.86-3.84 (m, 14H, H-3, H-5), 3.76-3.74 (m, 7H, OCH$_a$), 3.38-3.31 (m, 28H, H-4, H-2, CH$_2$N), 3.04-2.87 (m, 14H, H-6$_b$, H-6$_a$), 2.79-2.75 (m, 28H, CH$_2$CO$_2$, SCH$_2$CH$_2$N), 2.64-2.57 (m, 28H, CH$_2$SCH$_2$CH$_2$CO$_2$), 1.43 (s, 63H, C(CH$_3$)$_3$), 1.32-1.25 (m, 126H, CH$_2$×9), 0.87 (t, J=6.8 Hz, 21H, CH$_2$CH$_3$); $\delta_C$ (100 MHz, CDCl$_3$): 172.1 (CH$_2$C=O), 156.0 (NC=O), 101.7 (C-1), 86.2 (C-4), 80.9 (C-2), 73.4 (C(CH$_3$)$_3$), 73.1 (C-3), 71.8 (OCH$_2$), 71.1 (C-5), 65.0 (CO$_2$CH$_2$), 40.2 (CH$_2$N), 35.0 (SCH$_2$CH$_2$CO$_2$), 33.6 (C-6, SCH$_2$CH$_2$N), 32.0-22.8 (CH$_2$ alkyl, OCH$_2$CH$_2$, CH$_2$CO$_2$), 28.8, 28.7, 28.6 (C(CH$_3$)$_3$, OCH$_2$CH$_2$CH$_2$, CO$_2$CH$_2$CH$_2$), 14.3 (CH$_2$CH$_3$).

Heptakis[6-(N-Boc-2-amino-ethylthio)-6-deoxy-2-O-hexadecyloxycarbonylethylsulfanylpropyl]-β-cyclodextrin This compound was prepared from heptakis [2-O-allyl-6-(N-Boc-2-aminoethylthio)-6-deoxy]-β-cyclodextrin (0.4 g, 0.15 mmol) and hexadecyl-3-mercaptopropionate (1.1 g, 3.3 mmol) and AIBN (0.012 g, 0.1 mmol) dissolved in toluene (3 mL) were added to the solution, which was then degassed for 30 min with nitrogen. Irradiation for 24 h and column chromatography (SiO$_2$, cyclohexane-ethyl acetate 60:40) afforded product (0.46 g, 60%) as a colourless solid (Found C, 60.63; H, 9.24; N, 2.48; S, 9.03. C$_{245}$H$_{455}$O$_{56}$N$_7$S$_{14}$ requires C, 60.75; H, 9.47; N, 2.02; S, 9.27%). $\delta_H$ (500 MHz, CDCl$_3$) 5.29 (br s, 7H, NH), 4.92 (br s, 14H, H-1, OH-3), 4.09-4.02 (m, 21H, CO$_2$CH$_2$, OCH$_b$), 3.86-3.82 (m, 14H, H-3, H-5), 3.77-3.73 (m, 7H, OCH$_a$), 3.38-3.31 (m, 28H, H-4, H-2, CH$_2$N), 3.05-2.89 (m, 14H, H-6$_b$, H-6$_a$), 2.78-2.74 (m, 28H, CH$_2$CO$_2$, SCH$_2$CH$_2$N), 2.64-2.57 (m, 28H, CH$_2$SCH$_2$CH$_2$CO$_2$), 1.90-1.85 (m, 14H, OCH$_2$CH$_2$), 1.64-1.58 (m, 14H, CO$_2$CH$_2$CH$_2$), 1.43 (s, 63H, C(CH$_3$)$_3$), 1.32-1.25 (m, 182H, CH$_2$×13), 0.87 (t, J=6.9 Hz, 21H, CH$_2$CH$_3$); $\delta_C$ (125 MHz, CDCl$_3$) 172.1 (CH$_2$C=O), 156.0 (NC=O), 101.7 (C-1), 86.2 (C-4), 80.9 (C-2), 79.3 (C(CH$_3$)$_3$), 73.1 (C-3), 71.8 (OCH$_2$), 71.0 (C-5), 65.0 (CO$_2$CH$_2$), 40.2 (CH$_2$N), 35.0 (SCH$_2$CH$_2$CO$_2$), 33.6 (C-6, SCH$_2$CH$_2$N), 32.0-22.8 (CH$_2$ alkyl chain, OCH$_2$CH$_2$, CH$_2$CO$_2$), 14.4 (CH$_2$CH$_3$).

Heptakis[6-(N-Boc-2-amino-ethylthio)-6-deoxy-2-O-benzyloxycarbonylethylsulfanylpropyl]-β-cyclodextrin This compound was prepared as described from heptakis [2-O-allyl-6-(N-Boc-2-aminoethylthio)-6-deoxy]-β-cyclodextrin (0.3 g, 0.1 mmol) and benzyl-3-mercaptopropionate (0.47 g, 2.4 mmol). The reaction mixture was irradiated for 5 h. Column chromatography (SiO$_2$, cyclohexane-ethyl acetate 50:50) gave product (0.23 g, 52%) as a colourless resin (Found C, 55.88; H, 7.29; N, 1.94; S, 10.66. C$_{182}$H$_{273}$O$_{56}$N$_7$S$_{14}$ requires C, 55.99; H, 7.05; N, 2.51; S, 11.50%). 54500 MHz, CDCl$_3$) 7.36-7.29 (m, 35H, C$_6$H$_5$), 5.31 (br s, 7H, NH), 5.12 (s, 14H, CO$_2$CH$_2$), 4.92 (br s, 14H, H-1, OH-3), 4.04-4.00 (m, 7H, OCH$_b$), 3.86-3.83 (m, 14H, H-3, H-5), 3.75-3.71 (m, 7H, OCH$_a$), 3.39-3.30 (m, 28H, H-4, H-2, NCH$_2$), 3.05-2.87 (m, 14H, H-6$_b$, H-6$_a$), 2.79-2.74 (m, 28H, CH$_2$CO$_2$, SCH$_2$), 2.65-2.58 (m, 28H, SCH$_2$CH$_2$CO$_2$, OCH$_2$CH$_2$CH$_2$), 1.87-1.82 (m, 14H, OCH$_2$CH$_2$), 1.43 (s, 63H, C(CH$_3$)$_3$); $\delta_C$ (125 MHz, CDCl$_3$) 171.8 (CH$_2$CO$_2$), 156.0 (NCO$_2$), 136.0 (OCH$_2$CPH), 128.7, 128.38, 128.35 (Ph), 101.7 (C-1), 86.2 (C-4), 80.9 (C-2), 79.4 (C(CH$_3$)$_3$), 73.1 (C-3), 71.8 (OCH$_2$CH$_2$), 71.0 (C-5), 66.6 (CH$_2$Ph), 40.2 (NCH$_2$), 35.0 (SCH$_2$CH$_2$CO$_2$), 33.6 (SCH$_2$CH$_2$N, C-6), 29.8 (OCH$_2$CH$_2$), 28.64 (C(CH$_3$)$_3$), 28.58 (OCH$_2$CH$_2$CH$_2$), 27.0 (CH$_2$CO$_2$).

Heptakis[6-(N-Boc-2-amino-ethylthio)-6-deoxy-2-O-octylsulfanylpropyl]-β-cyclodextrin This compound was prepared from heptakis [2-O-allyl-6-(N-Boc-2-aminoethylthio)-6-deoxy]-β-cyclodextrin (0.14 g, 0.05 mmol) and 1-octyl thiol (0.21 mL, 1.1 mmol). The reaction mixture was irradiated for 1 h. Column chromatography (SiO$_2$, cyclohexane/ethyl acetate: 65:35) gave product (0.1 g, 51%) as a cloudy wax (Found C, 56.90; H, 8.77; N, 3.06. C$_{168}$H$_{315}$O$_{42}$N$_7$S$_{14}$ requires C, 56.77; H, 8.93; N, 2.76%). $\delta_H$ (500 MHz, CDCl$_3$) 5.31 (br s, 7H, NH), 4.93 (br s, 14H, H-1, OH-3), 4.08-4.03 (m, 7H, OCH$_b$), 3.87-3.83 (m, 14H, H-3, H-5), 3.79-3.74 (m, 7H, OCH$_a$), 3.38-3.32 (m, 28H, H-4, H-2, CH$_2$N), 3.06-2.87 (m, 14H, H-6$_b$, H-6$_a$), 2.74 (br s, 14H, SCH$_2$CH$_2$N), 2.59 (t, J=7.3 Hz, 14H, OCH$_2$CH$_2$CH$_2$), 2.51 (t, J=7.4 Hz, 14H, SCH$_2$CH$_2$), 1.90-1.85 (m, 14H, OCH$_2$CH$_2$), 1.60-1.54 (m, 14H, SCH$_2$CH$_2$), 1.44 (s, 63H, C(CH$_3$)$_3$), 1.39-1.28 (m, 70H, (CH$_2$×5), 0.88 (t, J=6.8 Hz, 21H, CH$_2$CH$_3$); $\delta_C$ (125 MHz, CDCl$_3$) 156.0 (C=O), 101.7 (C-1), 86.2 (C-4), 80.9 (C-2), 79.4 (C(CH$_3$)$_3$), 73.1 (C-3), 72.0 (OCH$_2$), 71.1 (C-5); 40.2 (CH$_2$N), 33.7 (C-6, SCH$_2$CH$_2$N), 32.3 (SCH$_2$(CH$_2$)n), 32.0, 29.42, 29.37, 22.8 (CH$_2$X4), 30.0 (OCH$_2$CH$_2$) 29.8 (SCH$_2$CH$_2$CH$_2$), 29.1 (SCH$_2$CH$_2$CH$_2$), 28.7 (OCH$_2$CH$_2$CH$_2$, C(CH$_3$)$_3$), 14.2 (CH$_2$CH$_3$).

Heptakis[6-(N-Boc-2-amino-ethylthio)-6-deoxy-2-O-dodecylsulfanylpropyl]-β-cyclodextrin This compound was prepared from heptakis [2-O-allyl-6-(N-Boc-2-aminoethylthio)-6-deoxy]-β-cyclodextrin (0.4 g, 0.15 mmol) and 1-dodecyl thiol (0.79 mL, 3.3 mmol). The reaction mixture was irradiated for 8 h (after 1 h the minimum amount of toluene was added to clear the solution). Column chromatography (SiO$_2$, cyclohexane/ethyl acetate: 65:35) gave product (0.34 g, 54%) as a colourless solid (Found C, 59.51; H, 9.31; N, 2.37; S, 11.07. C$_{196}$H$_{37}$O$_{42}$N$_7$S$_{14}$ requires C, 59.64; H, 9.47; N, 2.48; S, 11.37%). $\delta_H$ (500 MHz, CDCl$_3$) 5.30 (br s, 7H, NH), 4.93 (br s, 14H, H-1, OH-3), 4.07-4.03 (m, 7H, OCH$_b$), 3.86-3.83 (m, 14H, H-3, H-5), 3.78-3.73 (m, 7H, OCH$_a$), 3.38-3.31 (m, 28H, H-4, H-2, CH$_2$N), 3.05-2.87 (m, 14H, H-6$_b$, H-6$_a$), 2.74 (br s, 14H, SCH$_2$CH$_2$N), 2.58 (t, J=7.2 Hz, 14H, OCH$_2$CH$_2$CH$_2$), 1.59-1.54 (m, 14H, SCH$_2$CH$_2$(CH$_2$)$_n$), 1.44 (s, 63H, C(CH$_3$)$_3$), 1.38-1.34 (m, 14H, SCH$_2$CH$_2$CH$_2$), 1.31-1.26 (m, 112H, CH$_2$×8), 0.88 (t, J=6.9 Hz, 21H, CH$_2$CH$_3$); $\delta_C$ (125 MHz, CDCl$_3$) 156.1 (C=O), 101.8 (C-1), 86.3 (C-4), 81.0 (C-2), 80.0 (C(CH$_3$)$_3$), 73.3 (C-3), 72.2 (OCH$_2$), 71.2 (C-5), 40.4 (CH$_2$N), 33.8 (C-6, SCH$_2$CH$_2$N), 32.4 (SCH$_2$CH$_2$CH$_2$), 32.2, 29.96, 29.93, 29.90, 29.89, 29.86, 29.6, 29.3, 22.9 (CH$_2$×8), 30.1 (OCH$_2$CH$_2$), 28.8 (OCH$_2$CH$_2$CH$_2$, C(CH$_3$)$_3$), 14.3 (CH$_2$CH$_3$).

Heptakis[6-(N-Boc-2-amino-ethylthio)-6-deoxy-2-O-hexadecylsulfanylpropyl]-β-cyclodextrin This compound was prepared from heptakis [2-O-allyl-6-(N-Boc-2-aminoethylthio)-6-deoxy]-β-cyclodextrin (0.30 g, 0.1 mmol) and 1-hexadecyl thiol (0.5 g, 2 mmol). After irradiation for 2 h the minimum amount of toluene was added to clear the solution before irradiation for a further 22 h. Column chromatography (SiO$_2$, cyclohexane/ethyl acetate: 65:35) afforded product (0.3 g, 58%) as a colourless solid (Found C, 62.03; H, 9.76; N, 2.56; S, 10.10. C$_{224}$H$_{427}$O$_{42}$N$_7$S$_{14}$ requires C, 61.99; H, 9.92; N, 2.26; S, 10.34%). $\delta_H$ (500 MHz, CDCl$_3$) 5.30 (br s, 7H, NH), 4.93 (br s, 14H, H-1, OH-3), 4.06-4.03 (m, 7H, OCH$_b$), 3.86-3.83 (m, 14H, H-3, H-5), 3.78-3.73 (m, 7H, OCH$_a$), 3.37-3.31 (m, 28H, H-4, H-2, CH$_2$N), 2.58 (t, J=7.0 Hz, 14H, OCH$_2$CH$_2$CH$_2$), 2.50 (t, J=7.3 Hz, 14H, SCH$_2$(CH$_2$)$_n$), 1.90-1.84 (m, 14H, OCH$_2$CH$_2$), 1.59-1.53 (m, 14H, SCH$_2$CH$_2$(CH$_2$)$_n$), 1.44 (s, 63H, C(CH$_3$)$_3$), 1.38-1.25 (m, 182H, CH$_2$×13), 0.87 (t, J=6.9 Hz, 21H, CH$_2$CH$_3$); $\delta_C$ (125 MHz, CDCl$_3$) 156.1 (C=O), 101.8 (C-1), 86.2 (C-4), 81.0 (C(CH$_3$)$_3$), 79.5 (C-2), 73.2 (C-3), 72.2 (OCH$_2$), 71.1 (C-5), 40.3 (CH$_2$N), 33.8 (C-6, SCH$_2$CH$_2$N), 32.4 (SCH$_2$(CH$_2$)$_n$), 32.2, 30.0-29.3, 22.9 (CH$_2$ alkyl chain), 30.1 (OCH$_2$CH$_2$), 28.8 (C(CH$_3$)$_3$, OCH$_2$CH$_2$CH$_2$), 14.3 (CH$_2$CH$_3$).

Heptakis[6-(2-amino-ethylthio)-6-deoxy-2-O-methoxycarbonylethylsulfanylpropyl]-β-cyclodextrin hepta-N-trifluoroacetate To a stirred solution of the N-Boc derivative (0.2 g, 0.05 mmol) in CH$_2$Cl$_2$ (2 mL) was added TFA (0.23 mL, 2.95 mmol). The reaction mixture was stirred for 16 h at room temperature then concentrated under reduced pressure below 30° C. Size-exclusion chromatography on Sephadex LH-20-100 (MeOH) gave product (0.14 g, 77%) as a colourless solid. $\delta_H$ (500 MHz, CD$_3$OD) 5.07 (d, J=3.5 Hz, 7H, H-1), 4.07-4.03 (m, 7H, OCH$_b$), 3.94-3.90 (m, 14H, H-5, H-3), 3.84-3.80 (m, 7H, OCH$_a$), 3.70 (s, 21H, OCH$_3$), 3.57 (t, J=9.2 Hz, 7H, H-4), 3.45-3.42 (m, 7H, H-2), 3.21 (t, J=7.0 Hz, 14H, SCH$_2$CH$_2$N), 3.28 (d, J=13 Hz, 7H, H-6$_b$), 3.03-2.91 (m, 21H, CH$_2$N, H-6$_a$), 2.82-2.79 (m, 14H, CH$_2$CO$_2$), 2.78-2.64 (m, 28H, CH$_2$SCH$_2$CH$_2$CO$_2$), 1.91-1.86 (m, 14H, OCH$_2$CH$_2$); $\delta_C$ (125 MHz, CD$_3$OD) 174.2 (CH$_2$C=O), 163.4 (F$_3$CC=O), 118.5 (CF$_3$), 102.6 (C-1), 86.7 (C-4), 82.0 (C-2), 74.2 (C-3), 73.0 (C-5), 72.7 (OCH$_2$), 52.4 (OCH$_3$), 40.0 (CH$_2$N), 35.7 (SCH$_2$CH$_2$CO$_2$), 33.8 (C-6), 31.8 (SCH2CH$_2$N), 31.1 (OCH$_2$CH$_2$), 29.3 (OCH$_2$CH$_2$CH$_2$), 27.9 (CH$_2$CO$_2$).

Heptakis[6-(2-amino-ethylthio)-6-deoxy-2-O-hexyloxycarbonylethylsulfanylpropyl]-β-cyclodextrin hepta-N-trifluoroacetate This compound was prepared from the N-Boc derivative (0.135 g, 0.04 mmol). This yielded the TFA salt as a colourless solid which was then dissolved in methanol. The pH was adjusted to 2 with 0.1M HCl before the solvent was evaporated. Size-exclusion chromatography on Sephadex LH-20-100 (MeOH) gave product as a colourless solid (74 mg, 58%). $\delta_H$ (500 MHz, CD$_3$OD) 5.12 (d, J=3.5 Hz, 7H, H-1), 4.13-4.06 (m, 21H, CO$_2$CH$_2$, OCH$_b$), 3.94-3.81 (m, 21H, H-3, H-5, OCH$_a$), 3.56 (t, J=9.2 Hz, 7H, H-4), 3.45 (dd, J=3.5 Hz, J=9.6 Hz, 7H, H-2), 3.25-3.19 (m, 21H, CH$_2$N, H-6'), 3.09-2.98 (m, 21H, SCH$_2$CH$_2$N, H-6), 2.81 (t, J=7.1 Hz, 14H, CH$_2$CO$_2$), 2.74-2.63 (m, 28H, CH$_2$SCH$_2$CH$_2$CO$_2$), 1.90-1.86 (m, 14H, OCH$_2$CH$_2$), 1.69-1.64 (m, 14H, CO$_2$CH$_2$CH$_2$), 1.44-1.34 (m, 42H, CH$_2$×3), 0.94 (t, J=7.0 Hz, 21H, CH$_3$); $\delta_C$ (125 MHz, CD$_3$OD) 173.8 (C=O), 102.6 (C-1), 87.0 (C-4), 82.0 (C-2), 74.4 (C-3), 72.7 (C-5), 65.9 (OCH$_2$), 40.2 (CH$_2$N), 36.1 (SCH$_2$CH$_2$CO$_2$), 34.1 (C-6); 32.7, 26.7, 23.7 (CH$_2$×3), 31.7 (SCH$_2$CH$_2$N), 31.3 (OCH$_2$CH$_2$), 29.8 (CO$_2$CH$_2$CH$_2$), 29.3 (OCH$_2$CH$_2$CH$_2$), 28.0 (CH$_2$CO$_2$), 14.6 (CH$_3$).

Heptakis[6-(2-amino-ethylthio)-6-deoxy-2-O-dodecyloxycarbonylethylsulfanylpropyl]-β-cyclodextrin hepta-N-trifluoroacetate This compound was prepared from the N-Boc derivative (0.1 g, 0.02 mmol) with a reaction time of 24 h. Evaporation and drying in vacuo for 8 h gave 22 (84 mg, q.y.) as a cream solid. $\delta_H$ (500 MHz, CDCl$_3$) 8.00 (br s, NH$_2$, 14H), 4.91 (br s, 14H, H-1, OH-3), 4.12-4.06 (m, 21H, CO$_2$CH$_2$, OCH$_b$), 3.84-3.76 (m, 21H, H-3, H-5, OCH$_a$), 3.49-2.76 (br m, 70H H-4, H-2, CH$_2$N, H-6$_b$, H-6$_a$, SCH$_2$CH$_2$N, CH$_2$CO$_2$), 2.64-2.58 (m, 28H, CH$_2$SCH$_2$CH$_2$CO$_2$), 1.87 (br s, 14H, OCH$_2$CH$_2$), 1.64-1.59 (m, 14H, CO$_2$CH$_2$CH$_2$), 1.33-1.26 (m, 126H, CH$_2$×9), 0.88 (t, J=7 Hz, 21H, CH$_3$); $\delta_C$ (125 MHz, CDCl$_3$) 172.2 (C=O), 161.9 (CF$_3$C=O), 116.6 (CF$_3$), 101.7 (C-1), 73.3 (C-3), 71.8 (OCH$_2$), 71.5 (C-5); 65.0 (CO$_2$CH$_2$), 38.6 (CH$_2$N), 35.1, 32.1, 30.5, 29.8-29.4, 28.8, 28.6, 27.1, 26.1, 22.8 (C-6, SCH$_2$CH$_2$N, OCH$_2$CH$_2$, SCH$_2$CH$_2$CO$_2$, CH$_2$×10 alkyl chain), 14.2 (CH$_3$).

Heptakis[6-(2-amino-ethylthio)-6-deoxy-2-O-hexadecyloxycarbonylethylsulfanylpropyl]-β-cyclodextrin hepta-N-trifluoroacetate This compound was prepared from the N-Boc derivative (0.15 g, 0.031 mmol) with a reaction time of 24 h. Size-exclusion chromatography gave product (128 mg, q.y.) as a colourless solid. $\delta_H$ (500 MHz, CDCl$_3$) 8.00 (br s, 14H, NH$_2$), 4.92 (br s, 14H, H-1, OH-3), 4.09-4.02 (m, 14H, CO$_2$CH$_2$, OCH$_b$), 3.85-3.75 (m, 21H, H-3, H-5, OCH$_a$), 3.44-2.76 (br m, 70H, H-4, H-2, SCH$_2$CH$_2$N, H-6$_b$, H-6$_a$, CH$_2$CO$_2$), 2.63-2.58 (m, 28H, CH$_2$SCH$_2$CH$_2$CO$_2$), 1.88-1.86 (m, 14H, OCH$_2$CH$_2$), 1.65-1.59 (m, 14H, CO$_2$CH$_2$CH$_2$), 1.43-1.26 (m, 182H, CH$_2$×13), 0.88 (t, J=6.9 Hz, 21H, CH$_3$); $\delta_C$ (125 MHz, CDCl$_3$) 172.5 (C=O), 161.3 (CF$_3$C=O), 115.9 (CF$_3$), 101.6 (C-1), 85.5 (C-4), 80.6 (C-2), 73.2 (C-3), 71.9 (OCH$_2$), 71.7 (C-5), 65.2 (CO$_2$CH$_2$), 38.6 (CH$_2$N), 35.0, 32.1, 31.6, 30.5, 29.9-29.4, 28.8, 28.6, 27.7, 26.1, 25.3, 22.8 (C-6, SCH$_2$CH$_2$N, OCH$_2$CH$_2$CH$_2$, SCH$_2$CH$_2$CO$_2$, CH$_2$×14 alkyl chain), 14.2 (CH$_3$).

Heptakis[6-(2-amino-ethylthio)-6-deoxy-2-O-benzyloxycarbonylethylsulfanylpropyl]-β-cyclodextrin hepta-N-trifluoroacetate This compound was prepared from the N-Boc derivative (83 mg, 0.02 mmol) with a reaction time of 18 h. Size-exclusion chromatography on Sephadex LH-20-100 (MeOH) gave product (38 mg, 45%) as a colourless resin. $\delta_H$ (500 MHz, CD$_3$OD) 7.32-7.28 (m, 42H, C$_6$H$_5$), 5.09 (s, 14H, OCH$_2$Ph), 5.04 (s, 7H, H-1), 4.05-4.01 (m, 7H, OCH$_b$), 3.95 (t, J=9.0 Hz, 7H, H-3), 3.77-3.74 (m, 21H, H-5, OCH$_a$), 3.52 (t, J=9.0 Hz, 7H H-4), 3.40 (dd, J=3.2 Hz, J=9.6 Hz, 7H, H-2), 3.21-t, J=7.3 Hz, 14H, CH$_2$N), 3.08 (d, J=13.3 Hz, 7H, H-6$_b$), 3.03-2.91 (m, 21H, SCH$_2$CH$_2$N, H-6$_a$), 2.75 (t, J=7.4 Hz, 14H, $CH_2CO_2$), 2.64-2.57 (m, 28H, $CH_2SCH_2CH_2CO_2$), 1.81-1.80 (m, 14H, $OCH_2CH_2$);

$\delta_C$ (125 MHz, $CD_3OD$) 173.4 ($CH_2C$=O), 163.1 ($CF_3C$=O), 137.6 ($CH_2CPh$), 129.6-129.2 (Ph), 116.8 ($CF_3$), 102.6 (C-1), 86.8 (C-4), 81.9 (C-2), 74.4 (C-3), 73.2 (C-5), 72.7 ($OCH_2$), 67.4 ($CH_2Ph$), 39.9 ($CH_2N$), 36.0 ($SCH_2CH_2CO_2$), 33.6 (C-6), 31.7 ($SCH_2CH_2N$), 31.3 ($OCH_2CH_2$), 29.2 ($OCH_2CH_2CH_2$), 27.8 ($CH_2CO_2$).

Heptakis[6-(2-amino-ethylthio)-6-deoxy-2-O-octylsulfanylpropyl]-β-cyclodextrin hepta-N-trifluoroacetate This compound was prepared from the N-Boc derivative (50 mg, 0.01 mmol) with a reaction time of 48 h. Size-exclusion chromatography on Sephadex LH-20-100 (MeOH) gave product (34 mg, 67%) as a glass-like solid. $\delta_H$ (500 MHz, $CD_3OD$) 5.07 (d, J=3.5 Hz, 7H, H-1), 4.12-4.08 (m, 7H, $OCH_b$), 3.94-3.80 (m, 21H, H-3, H-5, $OCH_a$), 3.54 (t, J=9.2 Hz, 7H, H-4), 3.44 (dd, J=3.6 Hz, J=9.6 Hz, 7H, H-2), 3.21-3.11 (m, 21H, $CH_2N$, H-$6_b$), 3.02-2.90 (m, 21H, $SCH_2CH_2N$, H-$6_a$), 2.70-2.61 (m, 14H, $OCH_2CH_2CH_2$), 2.56 (t, J=7.3 Hz, 14H, $SCH_2(CH_2)_n$), 1.92-1.86 (m, 14H, $OCH_2CH_2$), 1.65-1.59 (m, 14H, $SCH_2CH_2(CH_2)_n$), 1.44-1.34 (m, 70H, $CH_2\times5$), 0.95-0.91 (m, 21H, $CH_3$); $\delta_C$ (125 MHz, $CD_3OD$) 163.1 ($CF_3C$=O), 117.9 ($CF_3$), 102.6 (C-1), 86.9 (C-4), 81.9 (C-2), 74.5 (C-3), 73.2 (C-5), 72.8 ($OCH_2$), 40.1 ($CH_2N$), 33.8 (C-6), 33.1, 30.5, 30.4, 30.1, 23.8 ($CH_2\times5$), 33.0 ($SCH_2(CH_2)_n$), 31.9 ($SCH_2CH_2N$), 31.5 ($OCH_2CH_2$), 31.0 ($SCH_2CH_2(CH_2)_n$), 29.4 ($OCH_2CH_2CH_2$), 14.7 ($CH_3$).

Heptakis[6-(2-amino-ethylthio)-6-deoxy-2-O-dodecylsulfanylpropyl]-β-cyclodextrin hepta-N-trifluoroacetate This compound was prepared from the N-Boc derivative (0.2 g, 0.05 mmol) with a reaction time of 24 h. Evaporation, and drying under high vacuum for 8 h, gave product (164 mg, q.y.) as a glass-like solid. $\delta_H$ (500 MHz, $CDCl_3$) 8.00 (br s, 14H, $NH_2$), 4.91 (br s, 14H, H-1, OH-3), 4.04 (br s, 7H, $OCH_b$), 3.84-3.75 (br m, 21H, H-3, H-5, $OCH_a$), 3.41-2.75 (br m, 56H H-4, H-2, H-$6_b$, H-$6_a$, $SCH_2CH_2N$), 2.59 (t, J=7.2 Hz, 14H, $OCH_2CH_2CH_2$), 2.51 (t, J=7.3 Hz, 14H, $SCH_2(CH_2)_n$), 1.89-1.86 (m, 14H, $OCH_2$), 1.59-1.54 (m, 14H, $SCH_2CH_2$), 1.37-1.27 (m, 126H, $CH_2\times9$), 0.88 (t, 14H, J=6.9 Hz, $CH_3$); k (125 MHz, $CDCl_3$) 162.8 ($CF_3C$=O), 116.7 ($CF_3$), 101.7 (C-1), 85.7 (C-4), 80.6 (C-2), 73.3 (C-3), 72.1 ($OCH_2$), 71.6 (C-5), 38.7 ($CH_2N$), 32.3, 32.1, 30.5, 30.0, 29.8-29.2, 28.7, 22.9 (C-6, $SCH_2CH_2N$, $OCH_2CH_2CH_2$, $CH_2\times11$), 14.3 ($CH_3$).

Heptakis[6-(2-amino-ethylthio)-6-deoxy-2-O-hexadecylsulfanylpropyl]-β-cyclodextrin hepta-N-trifluoroacetate This compound was prepared from the N-Boc derivative (0.15 g, 0.04 mmol) with a reaction time of 16 h. The product was dried without heating to obtain product (126 mg, q.y.) as a cream solid. $\delta_H$ (500 MHz, $CDCl_3$) 7.81 (br s, 14H, $NH_2$), 4.91 (br s, 14H, H-1, OH-3), 4.02 (br s, 7H, $OCH_b$), 3.84-3.76 (br m, 21H, H-3, H-5, $OCH_a$), 3.43-2.71 (br m, 56H, H-4, H-2, H-$6_b$, H-$6_a$, $SCH_2CH_2N$), 2.58 (t, J=7 Hz, 14H, $OCH_2CH_2CH_2$), 2.50 (t, J=7.3 Hz, $SCH_2CH_2CH_2$), 1.87 (m, 14H, $OCH_2CH_2$), 1.60-1.54 (m, 14H, $SCH_2CH_2CH_2$), 1.37-1.26 (m, 182H, $CH_2\times13$), 0.88 (t, J=6.9 Hz, 21H, $CH_3$); $\delta_C$ (125 MHz, $CDCl_3$) 161.5 ($CF_3C$=O), 116.0 ($CF_3$), 101.6 (C-1), 85.6 (C-4), 80.6 (C-2), 73.2 (C-3), 72.1 ($OCH_2$), 71.7 (C-5), 38.6 ($CH_2N$), 32.3, 32.1, 31.6, 30.5, 29.9-29.2, 28.6, 22.8 (C-6, $SCH_2CH_2N$, $OCH_2CH_2CH_2$, $CH_2\times15$), 14.2 ($CH_3$).

TABLE

ESI high resolution mass measurements and their accuracies

| Compound | Chemical Formula | Calculated m/z $[M + 2H]^{2+}$ | Observed m/z $[M + 2H]^{2+}$ | Mass Measurement Accuracy (ppm) |
|---|---|---|---|---|
| $CH_3$ ester (19) | $C_{105}H_{189}O_{42}N_7S_{14}$ | 1334.9558 | 1334.9646 | 6.6 |
| C6 ester (20) | $C_{140}H_{259}O_{42}N_7S_{14}$ | 1580.2296 | 1580.2438 | 8.98 |
| C8 ester (21) | $C_{154}H_{287}O_{42}N_7S_{14}$ | 1678.3392 | 1678.3556 | 9.8 |
| C12 ester (22) | $C_{182}H_{343}O_{42}N_7S_{14}$ | 1874.5583 | 1874.5818 | 12.5 |
| C16 ester (23) | $C_{210}H_{399}O_{42}N_7S_{14}$ | 2070.7774 | 2070.7981 | 9.99 |
| C8 alkyl (25) | $C_{133}H_{259}O_{28}N_7S_{14}$ | 1426.2652 | 1426.2769 | 8.2 |
| C12 alkyl (26) | $C_{161}H_{315}O_{28}N_7S_{14}$ | 1622.4843 | 1622.4994 | 9.3 |
| C16 alkyl (27) | $C_{189}H_{371}O_{28}N_7S_{14}$ | 1818.7034 | 1818.7234 | 10.1 |

Example 3

Formation of bilayer vesicles of heptakis[6-(2'aminoethylthio)-2-O-octyloxycarbonylethylsulfanylpropyl]-β-cyclodextrin trifluoroacetic acid salt A stock solution of heptakis[6-(2'-aminoethylthio)-2-O-octyloxycarbonylethylsulfanylpropyl]-β-cyclodextrin trifluoroacetic acid salt was prepared by dissolving 10 mg of cyclodextrin in 1 mL of chloroform. A 50 μL aliquot of the stock solution (0.5 mg of cyclodextrin) was transferred to a glass vial. The solvent was evaporated slowly in order to form a thin film of cyclodextrin on the surface of the glass. Millipore water (5 mL) was then used to hydrate the film giving a cyclodextrin solution with a concentration of 0.1 mg/mL. The vial was capped and placed in an oven for 90 minutes at 60° C. The cyclodextrin solutions were then filtered through a 0.45 μm Gelman Acrodisk syringe filter into a fluorimeter cuvette to remove any particles and macro aggregates. DLS investigations of these solutions were carried out using a Malvern Autosizer 4700 equipped with an Innova 70 laser (488 nm) and a photomultiplier at an angle of 90°.

Sample solutions for TEM were prepared in a similar manner to the DLS samples. A drop of this solution was placed on a 200-mesh formvar/carbon copper grid and then blotted off after two minutes, then negatively stained with a drop of uranyl acetate (2% w/w) which was similarly blotted off after a period of 2 minutes. Aggregates were observed using a JEOL 2000 microscope at 80 kV as shown in FIG. 1.

Table 1 shows the results obtained from the DLS analysis of heptakis[6-(2"-aminoethylthio)-2-O-octyloxycarbonylethylsulfanylpropyl]-β-cyclodextrin trifluoroacetic acid salt.

TABLE 1

| $K_{count}$ | $Z_{average}$ (nm) | Polydispersity |
|---|---|---|
| Day 1 | | |
| 27.7 | 76 | 0.07 |
| 29.7 | 85 | 0.20 |
| Day 7 | | |
| 29.6 | 82 | 0.251 |

Example 4

Formation of nanoparticulate complexes of heptakis [6-(2'-aminoethylthio)-2-O-octyloxycarbonylethylsulfanylpropyl]-β-cyclodextrin trifluoroacetic acid salt and DNA The plasmid DNA used for the transfection studies was the pGL3luc plasmid. This plasmid contains the gene that encodes for the firefly luciferase enzyme which allows measurement of gene expression levels in cells.

The cyclodextrin was dissolved in chloroform to a concentration of 1 mg/mL. A slow stream of nitrogen was passed over the solution to remove solvent. The cyclodextrin was then reconstituted with a plasmid DNA solution to give a final cyclodextrin concentration of 1 mg/mL. The DNA concentration used depended on the ratio of cyclodextrin:DNA being studied. This cyclodextrin:DNA solution was then sonicated for 1 hour to facilitate size reduction.

FIG. 2 shows the TEM results of the formation of nanoparticulate complexes of the heptakis[6-(2'-aminoethylthio)-2-O-octyloxycarbonylethylsulfanylpropyl]-β-cyclodextrin trifluoroacetic acid salt. DNA complex using a JEOL 2000 microscope at 80 kV.

Example 5

Transfection of biological cells heptakis[6-(2'-aminoethylthio)-2-O-octyloxycarbonylethylsulfanylpropyl]-β-cyclodextrin trifluoroacetic acid salt Cos-7 cells were seeded at a density of 30,000 cells per well and grown in 24 well plates in media for 20-24 hours. Prior to transfection studies, the cells were rinsed with serum-free media and then incubated in serum-free media for 1 hour. Vector. DNA complexes were prepared in a final volume of 100 μL so that 1 μg of DNA complexed with the vectors at the desired mass ratio. This was then added to 400 μL of serum-free media and cells which was left at 37° C. for 4 hours. After this period serum containing media was added to each well so the cells grow in 10% FBS. Cells were cultured for a further 24 hours before they were harvested. Luciferase expression was then determined using a luciferase assay kit (Promega USA) and results were expressed as Relative Light Units (RLU) of luciferase per pg of protein (Bradford assay). The assay was carried out three times in all cases.

To assess the effects of serum on transfection the same method as described above was used, the only modification being the replacement of serum-free media with 10% FBS. For simulated intestinal fluid (SIF) studies the heptakis[6-(2'-aminoethylthio)-2-O-octyloxycarbonylethylsulfanylpropyl]-β-cyclodextrin trifluoroacetic acid salt. DNA complexes were incubated with SIF for 2 hours in a shaking incubator at 37° C. prior to being added to Cos-7 cells. Transfection was then assessed as described above.

The DNA was transfected into Cos-7 cells at heptakis[6-(2'-aminoethylthio)-2-O-octyloxycarbonylethylsulfanylpropyl]-β-cyclodextrin trifluoroacetic acid salt:DNA mass ratios of 10, 15 and 20. Both the commercial vector DOTAP and naked DNA were tested simultaneously. The heptakis[6-(2'-aminoethylthio)-2-O-octyloxycarbonylethylsulfanylpropyl]-β-cyclodextrin trifluoroacetic acid salt achieved transfection greater than DNA on its own and greater than DOTAP (1-oleoyl-2-[6-[(7-nitro-2-1,3-benzoxadiazol-4-yl)amino]hexanoyl]-3-trimethylammonium propane chloride salt) as shown in FIG. 3.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the appended claims.

The invention claimed is:

1. A macrocyclic derivative having a primary and a secondary side, the derivative consisting of units of the formula:

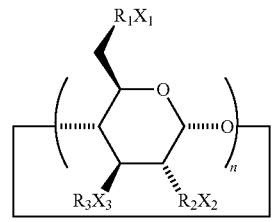

wherein the primary side is hydrophilic and is occupied by the $R_1X_1$ groups; and the secondary side is occupied by the $R_2X_2$ and the $R_3X_3$ groups;

wherein:

n is an integer from 6 to 8;

$X_1$ and $X_2$ are independently selected from the group comprising a simple covalent bond or an atom or radical with a valency of at least 2, and $X_3$ is O;

$R_1$ and $R_3$ are hydrophilic groups wherein $R_1$ comprises an amine group and $R_3$ is selected from H, $(CH_2)_{2-4}OH$, and $CH_2CH(CH_3)OH$;

$R_2$ is a lipophilic group comprising one or more of an aliphatic chain, an alicyclic, an aromatic, and a heterocyclic group or combinations thereof such that the number of lipophilic atoms in $R_2$ exceeds the number of non-lipophilic atoms in $R_3$ causing the secondary side to be lipophilic.

2. A macrocyclic derivative as claimed in claim 1, wherein the lipophilic group $R_2$ contains at least 4 carbon atoms.

3. A macrocyclic derivative as claimed in claim 1, wherein the lipophilic group $R_2$ further comprises one or more hetero atoms selected from the group comprising oxygen, nitrogen and sulfur.

4. A macrocyclic derivative as claimed in claim 1, wherein the lipophilic group $R_2$ further comprises a functional group selected from one or more of ethers, esters, carbamates, ketones, thioethers, thioesters, thioketones, sulfanyl, disulfide, sulfonyl, sulfoxy, sulfones, triazoles and amides.

5. A macrocyclic derivative as claimed in claim 1, wherein the $R_1$ amine group is selected from the group comprising $NH_2$; NHR where R is one or more of a methyl group, ethyl group, a branched or dendrimeric group comprising one to ten amine groups or a peptide containing basic amino acids, where one or more of the amino groups is optionally in its protonated form, preferably as a hydrohalide salt or trifluoroacetic acid salt.

6. A macrocyclic derivative as claimed in claim 1, wherein $X_1$ or $X_2$ further comprise one or more of ethers, esters, carbonates, ketones, thioethers, thioesters, thioketones, sulfanyl, disulfide, sulfonyl, sulfoxy, sulfones, triazoles and/or amides.

7. A colloid of layered-molecular structure formed by the self-assembly in aqueous solution of one or more of the macrocyclic derivatives as claimed in claim 1.

8. A surface-coated assembly formed from the self-assembly in aqueous solvent of one or more of the macrocyclic derivatives as claimed in claim 1, coated with a polyamine, peptide, protein, oligosaccharide, modified cyclodextrin oligosaccharide, polysaccharide, antibody and/or antibody fragment.

9. A surface-coated assembly formed from the self-assembly in aqueous solvent of one or more of the macrocyclic derivatives as claimed in claim 1 coated with a cholesterol, adamantane and/or other lipid derivative.

10. A composition comprising: one or more macrocyclic derivatives as claimed in claim 1 or a colloid of claim 7 or an assembly of claim 8 or 9; and (a) an oligonucleotide consisting of 2-50 nucleotides or nucleotide analogues, or (b) a nucleotide or nucleotide analogue.

11. A surface-coated assembly as claimed in claim 9, coated by host-guest inclusion or by amphiphilic or electrostatic interaction.

12. A surface-coated assembly as claimed in claim 8, coated by amphiphilic or electrostatic interaction.

13. A colloid layered molecular structure as claimed in claim 7 selected from a bilayer vesicle, micelle, monolayer on a supporting surface, or nanoparticle.

\* \* \* \* \*